(12) United States Patent
Iwamoto et al.

(10) Patent No.: US 11,833,256 B2
(45) Date of Patent: Dec. 5, 2023

(54) SELECTIVE RARγ LIGAND-LOADED NANOPARTICLES FOR MANIPULATION OF TARGETED BONE GROWTH

(71) Applicants: University Of Maryland, Baltimore, Baltimore, MD (US); Children's Hospital Of Philadelphia, Philadelphia, PA (US)

(72) Inventors: Masahiro Iwamoto, Baltimore, MD (US); Michael Chorny, Huntingdon Valley, PA (US)

(73) Assignees: University of Maryland, Baltimore, Baltimore, MD (US); The Children's Hospital of Philadelphia, Philadelphia, PA (US)

( * ) Notice: Subject to any disclaimer, the term of this patent is extended or adjusted under 35 U.S.C. 154(b) by 88 days.

(21) Appl. No.: 16/622,366

(22) PCT Filed: Jun. 20, 2018

(86) PCT No.: PCT/US2018/038504
§ 371 (c)(1),
(2) Date: Dec. 13, 2019

(87) PCT Pub. No.: WO2018/237004
PCT Pub. Date: Dec. 27, 2018

(65) Prior Publication Data
US 2020/0197321 A1    Jun. 25, 2020

Related U.S. Application Data

(60) Provisional application No. 62/522,307, filed on Jun. 20, 2017.

(51) Int. Cl.
| | | |
|---|---|---|
| *A61K 9/51* | (2006.01) | |
| *A61K 9/19* | (2006.01) | |
| *A61K 31/192* | (2006.01) | |
| *A61K 31/415* | (2006.01) | |
| *A61P 19/08* | (2006.01) | |

(52) U.S. Cl.
CPC .............. *A61K 9/5192* (2013.01); *A61K 9/19* (2013.01); *A61K 9/5153* (2013.01); *A61K 31/192* (2013.01); *A61K 31/415* (2013.01); *A61P 19/08* (2018.01)

(58) Field of Classification Search
CPC ...... A61K 9/5192; A61K 9/19; A61K 9/5153; A61K 31/192; A61K 31/415; A61K 47/34; A61P 19/08
See application file for complete search history.

(56) References Cited

U.S. PATENT DOCUMENTS

2003/0125252 A1* 7/2003 Underhill ................ A61P 35/00
562/450
2011/0293730 A1  12/2011 Kreuter et al.
2012/0195826 A1   8/2012 Baylatry et al.
2013/0296285 A1  11/2013 Alferiev et al.
2016/0038451 A1   2/2016 Makra

FOREIGN PATENT DOCUMENTS

WO    WO-03024473 A2 *  3/2003  ............. A61K 31/00

OTHER PUBLICATIONS

Zhang, Liangfang, et al. "Self-assembled lipid- polymer hybrid nanoparticles: a robust drug delivery platform." ACS nano 2.8 (2008): 1696-1702. (Year: 2008).*
Shimono, Kengo, et al. "Potent inhibition of heterotopic ossification by nuclear retinoic acid receptor-γ agonists." Nature medicine 17.4 (2011): 454-460. (Year: 2011).*
Tautzenberger A, Kovtun A, Ignatius A. Nanoparticles and their potential for application in bone. Int J Nanomedicine. 2012;7:4545-4557. (Year: 2012).*
Chakkalakal et al., Palovarotene Inhibits Heterotopic Ossification and Maintains Limb Mobility and Growth in Mice With the Human ACVR1(R206H) Fibrodysplasia Ossificans Progressiva (FOP) Mutation. J Bone Miner Res. Sep. 2016;31(9):1666-75. (Year: 2016).*
International Search Report and Written Opinion for International Patent Application No. PCT/US18/38504 dated Sep. 12, 2018, pp. 1-8.
Chandraratna, R.A.S., "Rational design of receptor-selective retinoids", Journal of the American Academy of Dermatology 1998, pp. S124-S128, vol. 39, No. 4, Part 2, Publisher: American Academy of Dermatology, Inc.
Chorny, M., et al., "Study of the drug release mechanism from tyrphostin AG-1295-loaded nanospheres by in situ and external sink methods," J. Control Release 2002, pp. 4014-4414, vol. 83, Issue 3.
Chorny, M., et al., "Lipophilic drug loaded nanospheres prepared by nanoprecipitation: effect of formulation variables on size, drug recovery and release kinetics," J. Control Release 2002, pp. 389-400, vol. 83, Issue 3.

(Continued)

*Primary Examiner* — Abigail Vanhorn
(74) *Attorney, Agent, or Firm* — Wolter Van Dyke Davis, PLLC; Eugene J. Molinelli; Martha Cassidy

(57) ABSTRACT

The invention relates to compositions and methods as part of a pharmacotherapeutic strategy that targets the endochondral ossification process in a pharmacologically selective and site-specific manner. A variety of orthopedic pathologies are caused by or associated with generalized or local dysregulation of endochondral ossification, for example trauma to the bone growth plate or diaphysis can cause a serious imbalance in bone growth, leading to progressive deformity that today can only be treated surgically. Dysregulated endochondral ossification is also behind heterotopic ossification, which arises in soft tissues and causes pain, decrease in mobility and other clinical problems. The invention therefore provides RARγ agonist and antagonist nanoparticle compositions for treating abnormal endochondral ossification and bone growth that can deliver robust local therapeutic control over a particular long bone's growth with a long-lasting effect.

3 Claims, 35 Drawing Sheets

(56) References Cited

OTHER PUBLICATIONS

Chorny, M., et al., "Biodegradable nanoparticles as drug delivery systems for parenteral administration," Tissue Engineering and Novel Delivery Systems 2003, pp. 393-422, Publisher: Marcel Dekker, Inc.

Chorny, M., et al., "Development and validation of a stability-indicating high performance liquid chromatographic assay for benoxinate," J. Pharm. Biomed. 2003, pp. 189-196, vol. 32, Issue 1.

Chorny, M., et al., "Adenoviral Gene Vector Tethering to Nanoparticle Surfaces Results in Receptor-Independent Cell Entry and Increased Transgene Expression," 2006, pp. 382-391, vol. 14, Issue 3.

Chorny, M., et al., "Magnetically driven plasmid DNA delivery with biodegradable polymeric nanoparticles," The FASBED Journal 2007, pp. 2510-2519, vol. 21, No. 10.

Chorny, M., et al., "Magnetically Responsive Biodegradable Nanoparticles Enhance Adenoviral Gene Transfer in Cultured Smooth Muscle and Endothelial Cells," Mol. Pharm. 2009, pp. 1380-1387, vol. 65, No. 5.

Chorny, M. et al., "Endothelial delivery of antioxidant enzymes loaded into nonpolymeric magnetic nanoparticles," J. Control Release 2010, pp. 144-151, vol. 146, No. 1.

Chorny, M., et al., "Targeting stents with local delivery of paclitaxel-loaded magnetic nanoparticles using uniform fields," Proc. Natl. Acad. Sci. USA 2010, pp. 8346-8351, vol. 107, No. 18.

Chorny, M., et al., "Formulation and In Vitro Characterization of Composite Biodegradable Magnetic Nanoparticles for Magnetically Guided Cell Delivery," Pharm. Res. 2012, pp. 1232-1241, vol. 29, No. 5.

Chorny, M., et al., "Site-specific gene delivery to stented arteries using magnetically guided zinc oleate-based hanoparticles loaded with adenoviral vectors," The FASEB Journal 2013, pp. 2198-2206, vol. 27, No. 6.

Hood, E.D., "Endothelial targeting of nanocarriers loaded with antioxidant enzymes for protection against vascular oxidative stress and inflammation," Biomaterials 2014, pp. 3708-3715, vol. 35, No. 11.

Iwamoto, M., et al., "Transcription Factor ERG Variants and Functional Diversification of Chondrocytes during Limb Long Bone Development," The Journal of Cell Biology 2000, pp. 27-40, vol. 150, No. 1.

Wamoto, M., et al., "Transcription Factor ERG and Joint and Articular Cartilage Formation during Mouse Limb and Spine Skeletogenesis," Dev. Biol. 2007, pp. 40-51, vol. 305, No. 1.

Peer, D., et al., "Nanocarriers as an emerging platform for cancer therapy," Nat. Nanotechnol. 2007, pp. 751-760, vol. 2, Issue 12.

Shimono, K., et al., "Potent inhibition of heterotopic ossification by nuclear retinoic acid receptor-gamma agonists," Nat Med 2011, pp. 454-460, vol. 17, No. 4.

Shimono, K., et al., "Inhibition of ectopic bone formation by a selective retinoic acid receptor alpha-agonist: a new therapy for heterotopic ossification ?." J Orthop Res 2010, pp. 271-277, vol. 28, No. 2.

Shore, E.M., "A recurrent mutation in the BMP type I receptor ACVR1 causes inherited and sporadic fibrodysplasia pssificans progressiva," Nature Genetics 2006, pp. 525-527, vol. 38, No. 5.

Thacher, S.M., "Therapeutic applications for ligands of retinoid receptors," Curr Pharm Des 2000, pp. 25-58, vol. 6, No. 1.

Williams, J.A., et al., "Retinoic acid receptors are required for skeletal growth, matrix homeostasis and growth plate function in postnatal mouse," Dev Biol 2009, pp. 315-327, vol. 328.

Williams, J.A., et al., "Endogenous retinoids in mammalian growth plate cartilage: analysis and roles in matrix homeostasis and turnover," J Biol Chem 2010, pp. 36674-36681, vol. 285, No. 47.

Shimono, K., et al., Supplementary Online Material for "Potent inhibition of heterotopic ossification by nuclear retinoic Receptor γ Agonists",Nat Med 2011, pp. 454-460, vol. 17, No. 4.

Jones, et al.; "Acute and Chronic Growth Plate Injuries"; Pediatr. Rev. 38:129-138, 2017.

Whitaker. et al.; "Lower extremity growth and deformity," Curr. Rev. Musculoskeletal Med. 9:454-461, 2016.

\* cited by examiner

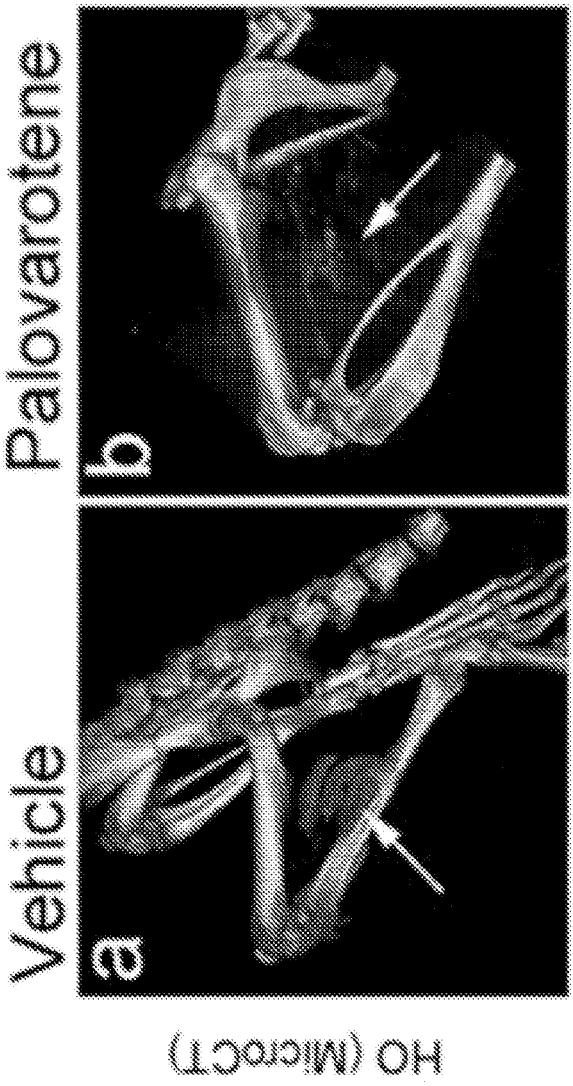

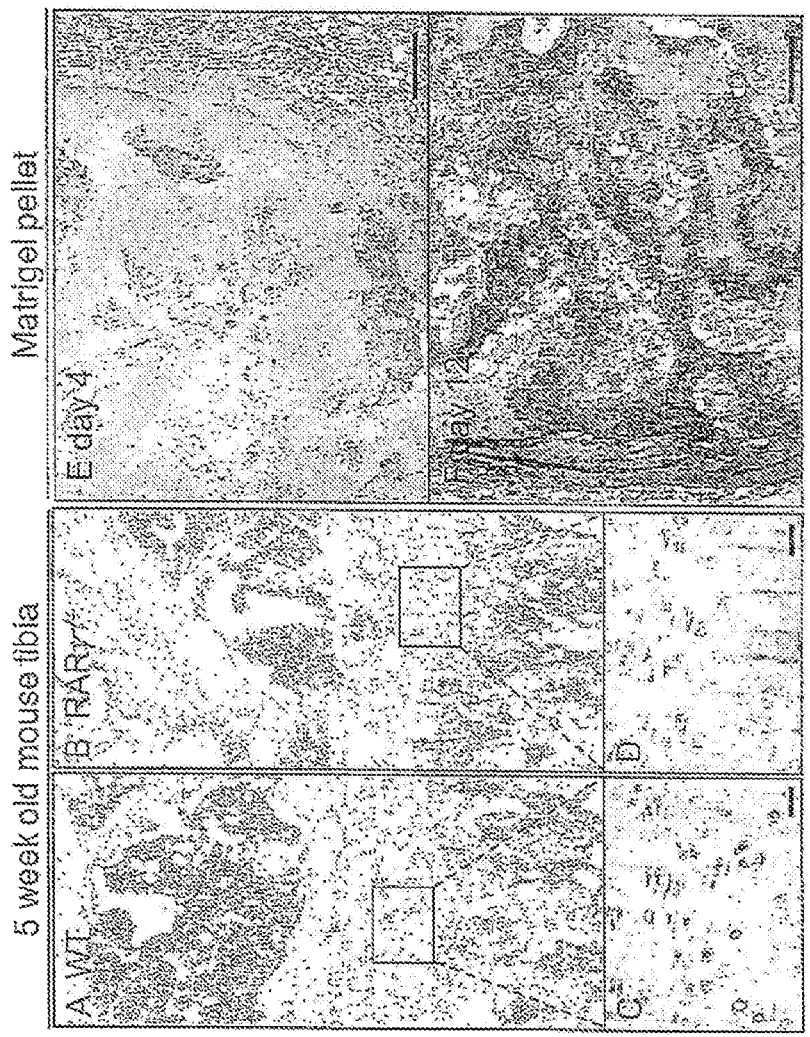

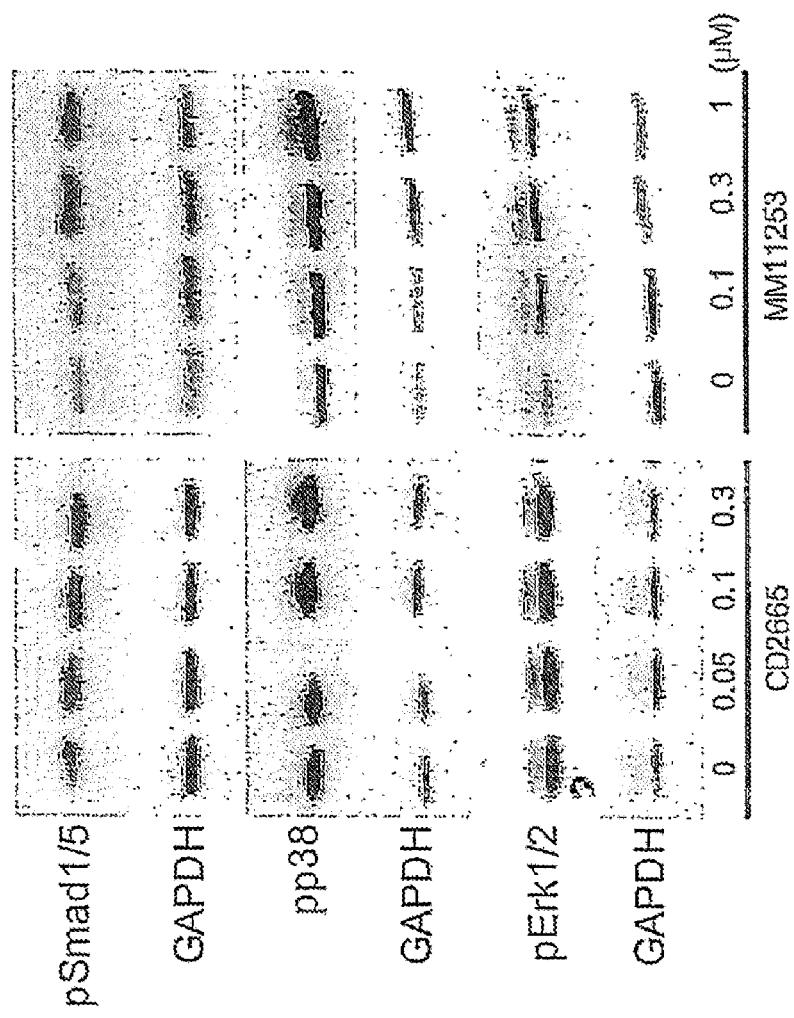

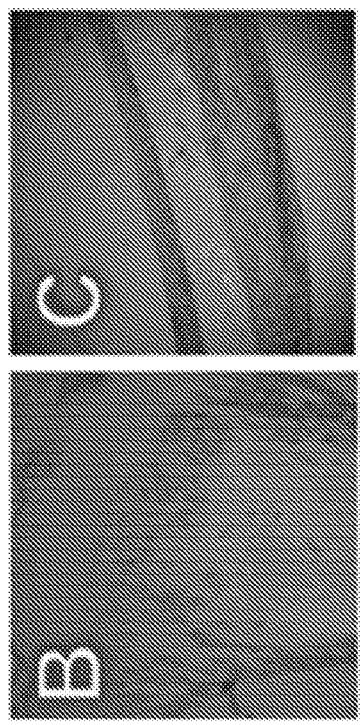
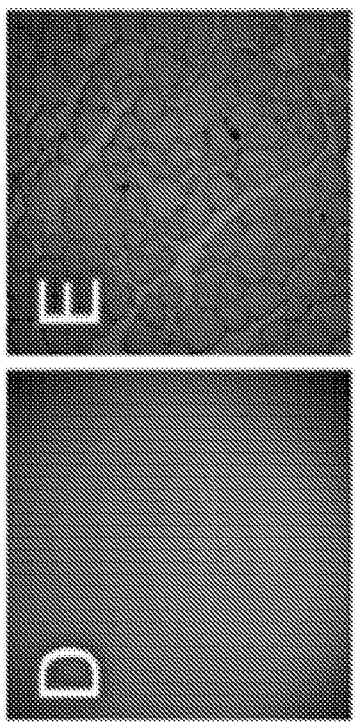
FIG. 9B  FIG. 9C
FIG. 9D  FIG. 9E

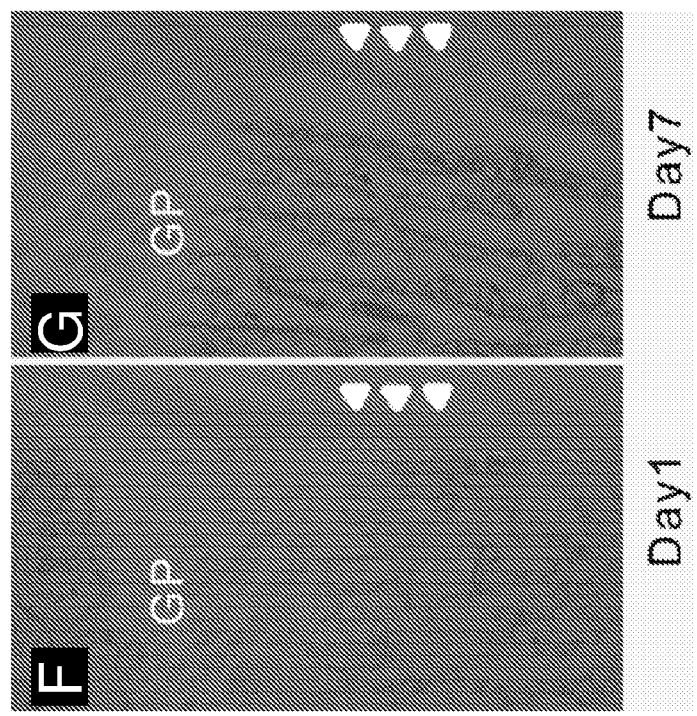

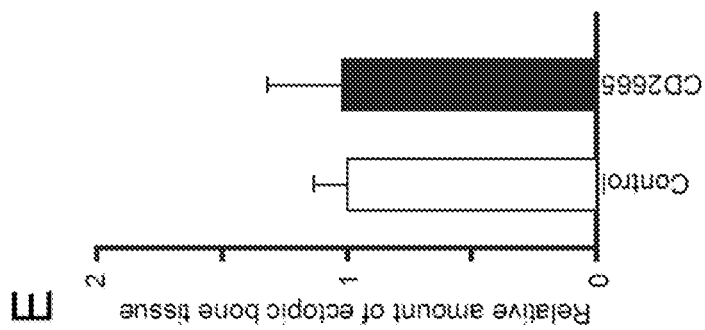
Fig. 13C
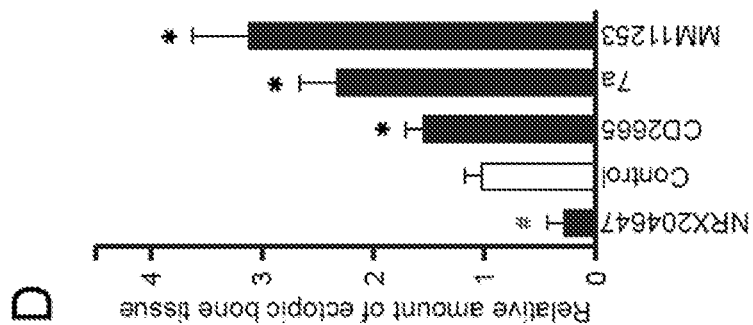
Fig. 13D    Fig. 13E
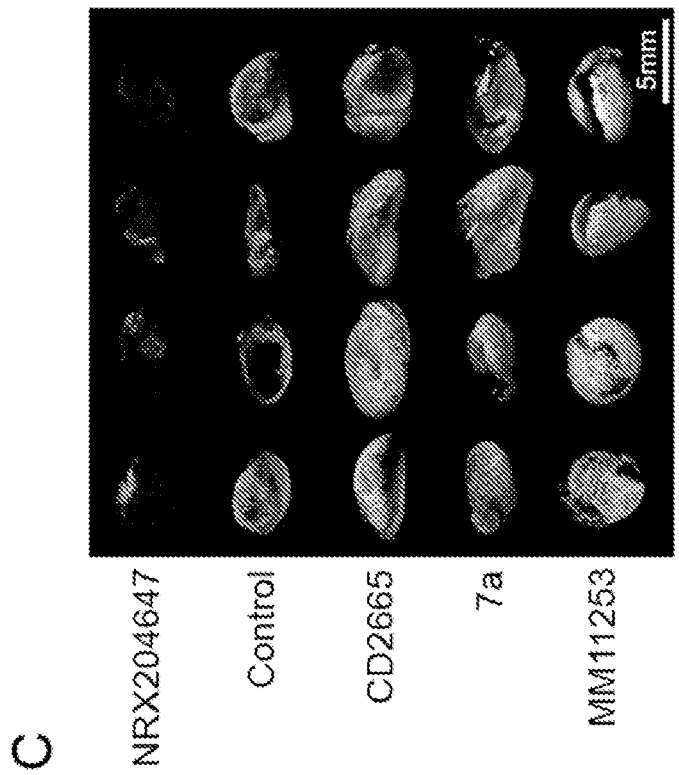

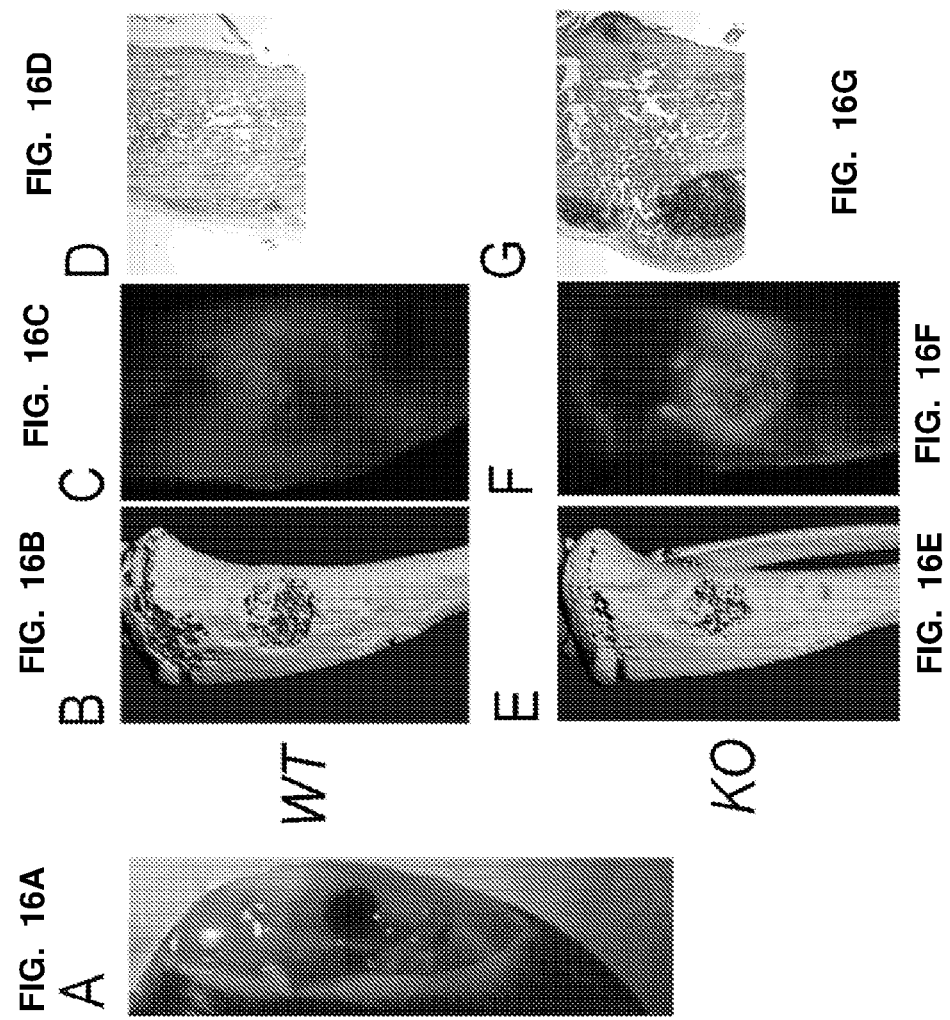

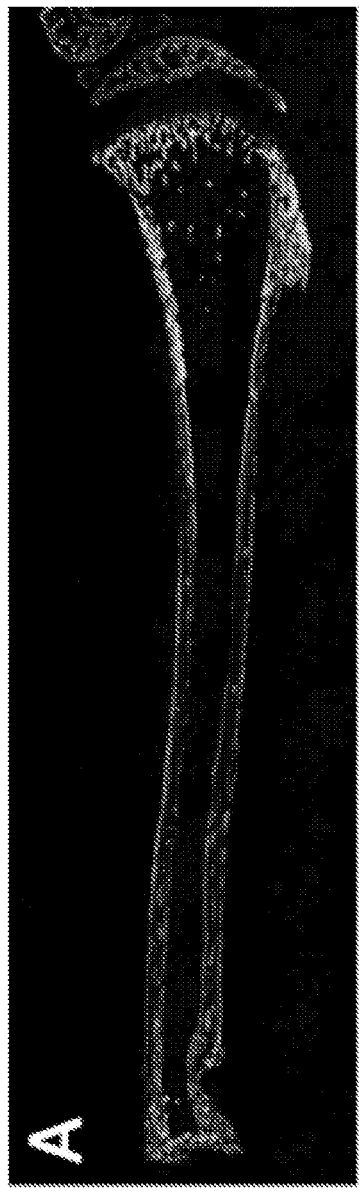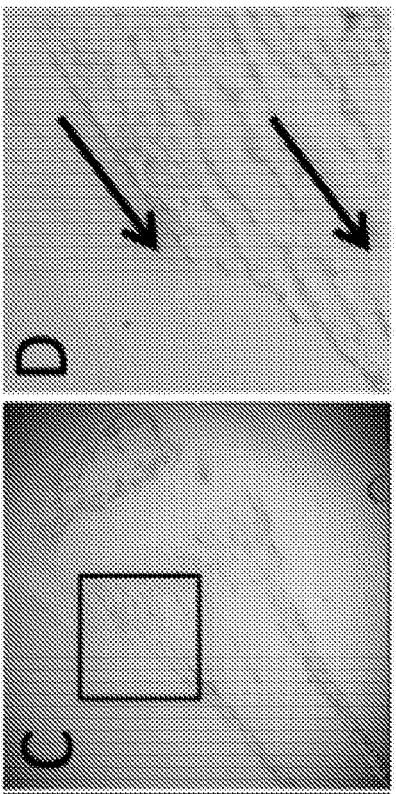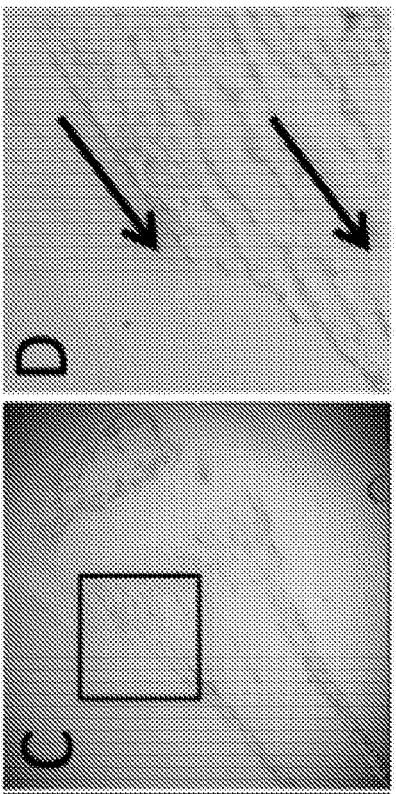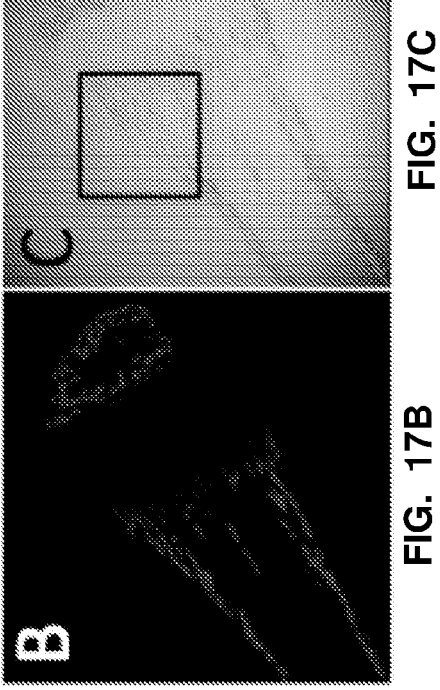
FIG. 17A
FIG. 17B
FIG. 17C
FIG. 17D

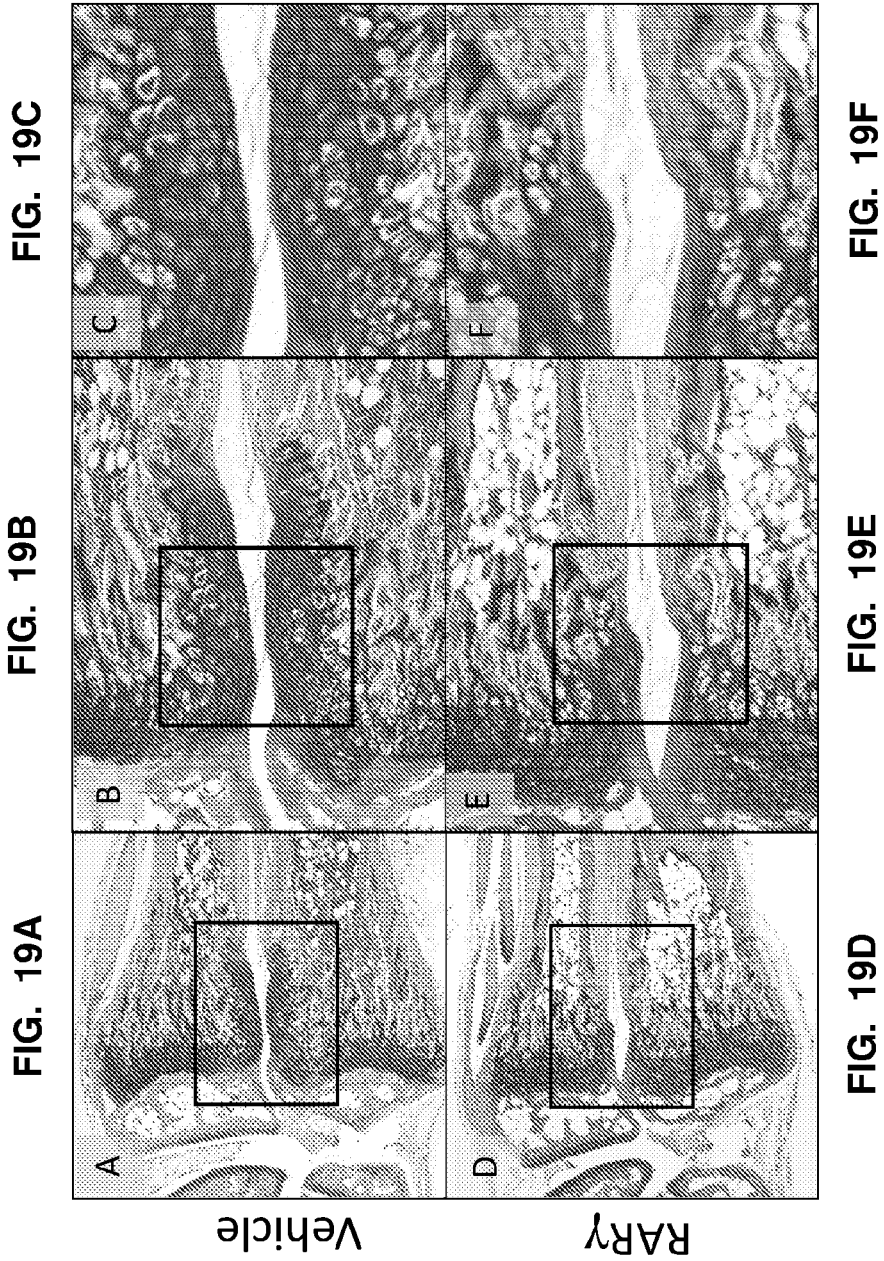

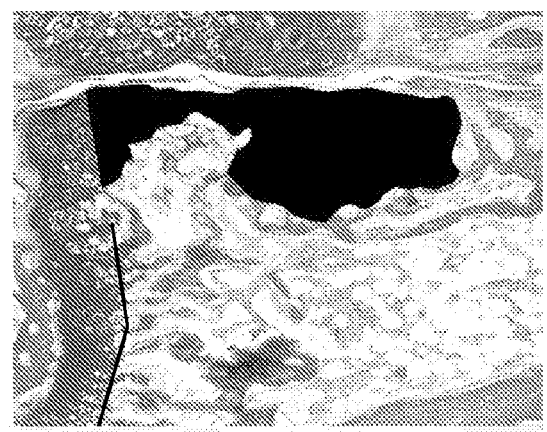
FIG. 20A RARγ
FIG. 20B Vehicle

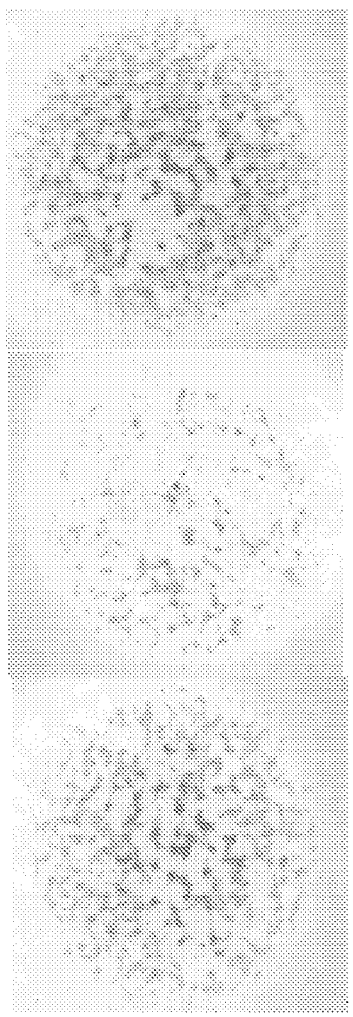

SELECTIVE RARγ LIGAND-LOADED NANOPARTICLES FOR MANIPULATION OF TARGETED BONE GROWTH

CROSS REFERENCE TO RELATED APPLICATIONS

This application is a 371 application of PCT Application No. PCT/US18/38504 filed Jun. 20, 2018 which claims the benefit of U.S. Provisional Application No. 62/522,307, filed 20 Jun. 2018, which is hereby incorporated by reference in its entirety.

STATEMENT OF GOVERNMENT SUPPORT

This invention was made with Government support under Grant No. AR056837, awarded by the National Institutes of Health. The Government has certain rights in the invention.

BACKGROUND

Field of the Invention

The invention relates to the field of medicine and in particular to longitudinal bone growth, including novel pharmacotherapeutic agents that target retinoic acid receptors which play key roles in the regulation of chondrogenesis and endochondral ossification. One such agent is a biodegradable nanoparticle complexed with potent a RARy agonist or antagonist.

Background of the Invention

Growth of endochondral skeletal structures occurs through a process of proliferation, matrix production and maturation of chondrocytes in growth-plate and the replacement of cartilage with bone. Abnormalities in any of the above functions can lead to skeletal abnormalities including dwarfism, growth imbalance, chondrodysplasia, and delayed fracture repair. The complex differentiation process of chondrocytes is regulated by a number of systemic and local factors. Growth-plate chondrocytes are able to terminally differentiate in vitro and induce cartilage matrix calcification by themselves. However, mineralization of cartilage-matrix is not an autonomous physicochemical event but a biological process, regulated by number of growth factors, hormones and morphogenetic regulators.

Endochondral ossification plays an essential role in normal longitudinal bone growth. Longitudinal bone growth starts with formation of primordial cartilage at future skeleton positions, providing a template of the axial and appendicular bones to the body. The developing cartilage then organizes into a unique structure, called growth plate (GP), where chondrocytes undergo a series of functional changes: active proliferation, abundant production of cartilage matrix and terminal differentiation characterized by matrix remodeling and mineralization or calcification. The growth plate then is invaded by newly formed blood vessels and osteoclasts, and eventually replaced with bone. Regulation of these processes in vivo is extremely complex, both in space and time, and they are thought to be regulated by very complex interactions between cells and growth factors, between cells and surrounding extracellular matrix components, and by cell-cell interactions. The rate and extent of endochondral ossification progress are essential determinants of normal skeletal growth.

A variety of orthopedic pathologies are caused by or associated with generalized or local dysregulation of endochondral ossification. Fractures in the growth plate (GP) can impair this process, resulting in stunted bone because endochondral ossification in GP is the main mechanism of longitudinal bone growth. In contrast, diaphyseal fractures may cause excessive bone growth, presumably due to regional activation of the GP function. Both conditions can trigger imbalance in length and shape between counterpart bones or among neighboring bones, leading to progressive deformity of the skeleton and significant physical problems. Fractures in growing children therefore require careful follow-up for their impact on bone growth. At present, surgery is the only means to locally correct deformities due to impaired bone growth. Such surgical procedures are highly invasive and impose a significant clinical and cost burden, warranting the development of alternative therapies sparing many patients the need for complex and costly surgical interventions.

Dysregulation of endochondral ossification may cause or accompany a wide range of orthopedic problems. Heterotopic ossification (HO) is pathological formation of endochondral bones in the soft tissue that is triggered by extrinsic factors such as trauma, major surgical interventions or severe burns, and intrinsic factors such as genetic mutations of Activin receptor type I (ACVRI) as seen in fibrodysplasia ossificans progressiva (FOP) disease. Both genetic and acquired HO often lead to severe clinical problems. There is no effective drug for this condition after the acute inflammation phase.

Induction or inhibition of sufficient bone formation at specific targeted anatomical sites has been a long sought-after goal in the treatment of various skeletal conditions, including surgical or traumatic bone defects and non-union fracture, destruction of bone by tumor, and various disease conditions, including heterotropic ossification (HO). Bone morphogenetic proteins (BMPs) and other bone inductive materials singly or in combination have been in use for nearly two decades to induce bone growth and are clinically proven to improve bone repair in some cases. Their use, however, still faces problems including high cost, limited effectiveness and suboptimal repair bone quality. In addition, studies have reported that the use of large doses of BMP can cause complications such as excess or heterotopic ossification, local inflammation, loosening of the fixative device due to bone resorption, and increased cancer risk. Clearly there is a need to develop additional and safer treatment strategy for bone repair and regeneration that is local, and site-specific, and can be tailored to the exact needs of the patient.

SUMMARY OF THE INVENTION

The invention relates to compositions and methods as part of a pharmacotherapeutic strategy that targets the endochondral ossification process in a pharmacologically selective and site-specific manner. Endochondral ossification plays a key role in normal skeletal formation. Its dysregulation (locally or generally) is associated with a variety of orthopedic pathologies, including trauma to the growth plate or diaphyseal fractures and heterotopic ossification (HO). The invention therefore provides RARy agonists and antagonists for the treatment of abnormal endochondral ossification and bone growth, and for treatment of osteochondroma, that are delivered in a nanoparticle formulations that can deliver robust and local therapeutic control over a particular long bone's growth or a particular area of a long bone's growth with a long-lasting effect. The treatment is highly site-specific and minimizes drug dissemination.

Specifically, the invention provides a pharmaceutical composition for comprising a poly(D,L-lactide) nanoparticle loaded with an RARγ modifying agent. In some embodiments the pharmaceutical composition is a lyophilized nanoparticle pharmaceutical composition made according to the process steps of: (a) dissolving an RARγ modifying agent in an organic solvent to form a solution; (b) adding poly(D,L-lactide) to the solution at a ratio of 0.25:100 w/w to 40:100 w/w RARγ modifying agent:poly(D,L-lactide) to form a mixture; (c) emulsifying the mixture in deionized water containing 10 mg/mL human serum albumin, at a ratio of about 8:10 v/v mixture:water; (d) removing the organic solvent to form a particle suspension; (e) adding about 200-3000 mg/mL human serum albumin and 500-5000 mg/mL glucose to the particle suspension; (f) optionally filtering the particle suspension; (g) filtering the particle suspension through a 5.0 μm sterile filter to produce a filtrate; (h) lyophilizing the filtrate; and (i) optionally storing the lyophilized filtrate. In some preferred embodiments, the lyophilized filtrate is resuspended in sterile, deionize water for use. In some embodiments, the organic solvent is selected from the group consisting of 1:7 ethanol:chloroform, 1:7 ethanol:dichloromethane, 1:7 ethanol:ethyl acetate, and any mixture thereof. Further, the organic solvent can be removed by evaporation.

Preferably, the RARγ modifying agent:poly(D,L-lactide) ratio is 20:100 w/w. Making the lyophilized nanoparticle pharmaceutical composition also can include a step of adding about 2000 mg/mL human serum albumin and 4000 mg/mL glucose to the particle suspension.

In some embodiments, the RARγ modifying agent is an RARγ agonist or an RARγ antagonist.

The invention also includes a method of treating dysregulation of endochondrial ossification in a subject in need thereof, comprising administering the lyophilized nanoparticle pharmaceutical composition discussed above to the subject. Administering the lyophilized nanoparticle pharmaceutical composition to the subject can be by local injection into the bone at or near the bone defect.

The invention also includes a method of treating a growth imbalance in a subject in need thereof, comprising administering the lyophilized nanoparticle pharmaceutical composition as discussed herein to the subject by local injection to an area of bone requiring growth inhibition, a method of treating a growth imbalance in a subject in need thereof, comprising administering the lyophilized nanoparticle pharmaceutical composition as discussed herein to the subject by local injection to an area of bone requiring growth enhancement, a method of treating an osteochondroma in a subject in need thereof, comprising administering the lyophilized nanoparticle pharmaceutical composition as discussed herein to the subject by local injection into the osteochondroma, a method of retarding bone growth in a discrete area of bone in a subject in need thereof, comprising administering the lyophilized nanoparticle pharmaceutical composition as discussed herein to the subject by local injection to the discrete area, a method of enhancing bone growth in a discrete area of bone in a subject in need thereof, comprising administering the lyophilized nanoparticle pharmaceutical composition as discussed herein to the subject by local injection to the discrete area, and a method of treating acquired or genetic heterotropic ossification in a subject in need thereof, comprising administering the lyophilized nanoparticle pharmaceutical composition as discussed herein by direct injection to an area of abnormal bone growth or an area of acute inflammation likely to develop abnormal bone growth.

DESCRIPTION OF THE FIGURES

FIGS. 5A-5B are a set of photographs of Acvr1cR206H/+ mutant mice without (FIG. 5A) and with (FIG. 5B) palovarotene.

FIG. 7A and FIG. 7B show immunohistochemical detection of RARγ in growth plate in 5-week-old wild-type and RARγ null mice, respectively. Bar=50 μm.

FIG. 7C and FIG. 7D show higher magnification of the indicated areas.

FIG. 7E and FIG. 7F show immunohistochemical detection of RARγ in BMP-Matrigel™ pellets 4 days and 12 days after implantation, respectively. Bar=50 μm.

FIG. 8A is an immunoblot showing the effects of RARγ antagonist treatment on levels of phosphorylated Smad1/5, p38 and Erk1/2 in the presence of retinoid antagonists and rhBMP-2.

FIG. 9B and FIG. 9C show the distribution of fluorescently-labeled NPs (~5 μg) in bone marrow space 2 weeks after injection.

FIG. 9D and FIG. 9E show the distribution of fluorescently-labeled NPs in a skeletal muscle 2 weeks after injection.

FIG. 9F and FIG. 9G show the distribution of labeled NPs in the vicinity of the growth-plate 1 and 7 days after injection.

FIG. 13C is a set of μCT images of ectopic tissue masses harvested on day 12 from Matrigel™ injection. Four repeat samples from each treatment group are shown.

FIG. 13D is a set of histograms showing the calculated amounts of ectopic bone volume expressed as BV/TV.

FIG. 13E is a set of histograms showing that CD2665 treatment had no effect on ectopic bone formation in RARγ-null mice. The Y-axis indicates the relative amount of bone compared to control. N=8.

FIG. 16A is a photograph showing the round hole made on the medial aspect of adult mouse tibias using a 22 gauge needle and dental carbide bur.

FIG. 16B, FIG. 16C, and FIG. 16D show μCT images of tibias on day 14 post-surgery, fluorescent macroscopic images of calcein-labeled tibias on day 14 post-surgery; and Alcian blue and eosin staining of tibia sections on day 7 from surgery, respectively in wild-type mice.

FIG. 16E, FIG. 16F, and FIG. 16G show the same information for KO (RARγ-null) mice.

FIG. 17A is a photograph showing fluorescence in mouse tibia after receiving xylenol orange 90 mg/kg on day 17 and calcein 30 mg/kg on day 25 by IP injection. The tibia was collected on day 27.

FIG. 17B, FIG. 17C, and FIG. 17D are photographs of mouse tibia from P10 mice after receiving xylenol orange 90 mg/kg by IP injection. Tibias were collected on day 12. FIG. 17B shows fluorescence; FIG. 17C shows a superimposed image of fluorescent and bright filed image; and FIG. 17D shows a higher magnification of the indicated area in FIG. 17C.

FIGS. 19A-19F are a set of photographs showing osteochondromas forming in the ulna and radius in the hereditary multiple exostasis (HME) mouse model. FIG. 19A, FIG. 19B, and FIG. 19C show vehicle control; FIG. 19D, FIG. 19E, and FIG. 19F show RARγ agonist-treated.

FIGS. 20A-20B are a set of photographs showing the defined regions of osteochondromas for quantitative analysis. FIG. 20A: RARγ; FIG. 20B: control.

FIG. 21B: control and Ext mutant: Control genotype mice and HME genotype mice.

FIGS. 22A-22C are a set of photographs showing the effects of RA and AGN194310 on cartilage matrix production in mouse limb bud cultures. FIG. 22A: control; FIG. 22B: RA (agonist); FIG. 22C: AGN194310 (pan-agonist).

DETAILED DESCRIPTION

1. Definitions

Figures 1A, 1B, 1C, 1D:
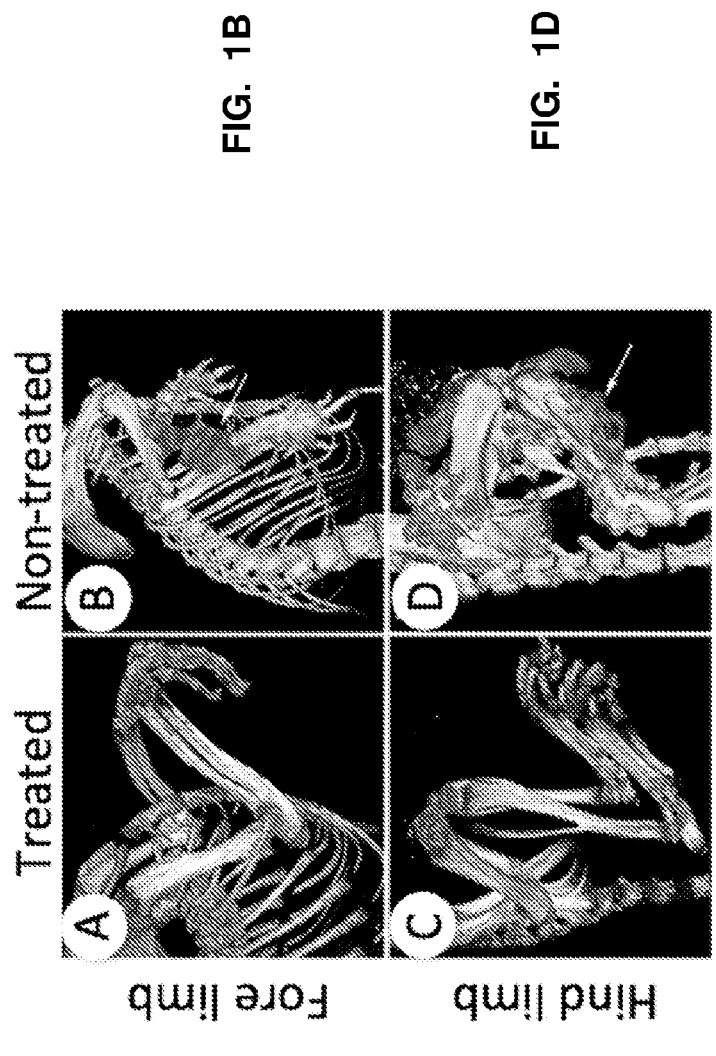
FIGS. 1A-1D is a set of photographs showing the fore limb (FIG. 1A and FIG. 1B) and hind limb (FIG. 1C and FIG. 1D) of mouse skeleton from FOP model mice, treated or non-treated as indicated, by oral administration of palovarotene.

Unless otherwise defined, all technical and scientific terms used herein are intended to have the same meaning as commonly understood in the art to which this invention pertains and at the time of its filing. Although various methods and materials similar or equivalent to those described herein can be used in the practice or testing of the present invention, suitable methods and materials are described below. However, the skilled artisan should understand that the methods and materials used and described are examples and may not be the only ones suitable for use in the invention. Moreover, it should also be understood that as measurements are subject to inherent variability, any temperature, weight, volume, time interval, pH, salinity, molarity or molality, range, concentration and any other measurements, quantities or numerical expressions given herein are intended to be approximate and not exact or critical figures unless expressly stated to the contrary. Hence, where appropriate to the invention and as understood by those of skill in the art, it is proper to describe the various aspects of the invention using approximate or relative terms and terms of degree commonly employed in patent applications, such as: so dimensioned, about, approximately, substantially, essentially, consisting essentially of, comprising, and effective amount. Unless defined otherwise, all technical and scientific terms used herein have the same meaning as commonly understood by one of ordinary skill in the art.

The term "about," as used herein, means plus or minus 10 percent of the recited value.

As the term is used herein, a "subject in need" includes any animal, preferably a mammal, including mammals such as a human, a laboratory animal, a companion animal, and a livestock animal that is suffering from dysregulation of endochondrial ossification, or a subtype of dysregulation of endochondrial ossification, or is suspected of suffering from dysregulation of endochondrial ossification. Such dysregulation of endochondrial ossification includes, but is not limited to: growth imbalance, skeletal deformity, mal-alignment, fracture or other injury to growth plate; fracture or other injury to the diaphysis of a bone in a growing subject;

HO, FOP, and the like, and osteochondroma. Preferably, the subject is human, however the invention contemplates treatment of animals such as rats, mice and rabbits, livestock such as cattle, sheep, pigs and the like, and companion animals such as dogs, cats and other pets.

As used herein, the term "treatment" refers to administration of the compounds or compositions of the invention to a subject in need wherein the condition is ameliorated, improved or cured, temporarily or permanently. Treatment can include a single administration or multiple administrations, over any period of time.

As used herein, the term "dysregulation of endochondral ossification" refers to any acquired or genetic condition or disorder, including trauma, that involves an unwanted change in, imbalance of length and/or alignment of the skeleton, skeletal deformity, or abnormal endochondral bone formation, delayed or non-union fractures, and includes but is not limited to posttraumatic or congenital heterotropic ossification such as fibrodysplasia ossificans progressiva and progressive osseous heteroplasia, chondrodysplasia, cartilagenous tumors such as osteochondroma, enchondroma, and chondrosarcoma and the like.

As used herein, the term "pharmaceutical composition" refers to a pharmaceutical agent, for example an RARγ modifying agent, and a pharmaceutically acceptable carrier.

The terms "pharmaceutically acceptable carrier," "pharmaceutically acceptable excipient," or "pharmaceutically acceptable vehicle" refer to any convenient solvent or suspending liquid, or any compound or group of compounds that is not toxic and that does not destroy or significantly diminish the pharmacological activity of the therapeutic agent with which it is formulated. Such pharmaceutically acceptable carriers or vehicles encompass any of the standard pharmaceutically accepted solid, liquid, or gaseous carriers known in the art, such as those discussed in the art.

As used herein, the term "RARγ modifying agent" refers to an RARγ agonist, an RARγ partial agonist, an RARγ antagonist, an RARγ blocker, an RARγ binder, and the like.

2. Overview

Retinoic acid (RA), the major active metabolite of retinol, plays important roles in embryonic development, organogenesis, and homeostasis of a variety of tissues. RA is one of key regulators of skeletal patterning during embryogenesis and regulates cartilage and bone development and homeostasis. It acts primarily by binding to its nuclear retinoic acid receptors (RARs). The RARs heterodimerize with retinoid X receptors (RXRs) and regulate cell function through direct activation of target gene expression and cross-talks with other signaling pathways. Mammals have three RAR isotypes (RARα, RARβ and RARγ) and three RXR isotypes (RXRα, RXRβ and RXRγ) that form a variety of heterodimer combinations and can exert different functions. Overall, the specificity and magnitude of RA action are controlled by the temporospatial patterns of expression of RARs and RXRs and the endogenous cellular levels of RA. RARγ is the major receptor to mediate anti-chondrogenic action of RA. Research presented here shows that pharmacological modulation of RARγ effectively blocks HO in animal models without serious side effects, and has enhancing (antagonist) or retarding (agonist) effects on bone growth after local delivery. The invention here relates to a drug-based therapy to locally control the endochondral ossification process and thereby correct bone growth imbalance and heterotopic ossification, or any dysregulation of endochondrial ossification.

3. Summary of Results

The effects of RARγ agonists and antagonists according to the invention on endochondrial ossification, as demonstrated in this application include:
1. RARγ agonists are potent inhibitors of chondrogenesis; in cartilage, RARγ agonists reduce chondrocyte proliferation, reduce matrix production, and stimulate cartilage matrix breakdown to reduce cartilage size and bone growth.
2. RARγ antagonists promote cartilage growth and bone growth.
3. RARγ ligand NPs are retained locally at the injection site and release active drug for a prolonged time period.
4. Local administration of RARγ ligand NPs, allows the practitioner to produce long-acting, site-specific effects on bone growth while minimizing systemic effects.
5. Administration of RARγ agonists is useful as a treatment for osteochondroma, a cartilage tumor.

4. Embodiments of the Invention

A. Introduction

Presently, there is a great need in the art for a pharmacotherapeutic strategy for targeting the endochondral ossification (EO) process with spatiotemporal control. Accurate regulation of endochondral ossification is essential for musculoskeletal tissues. It governs normal skeletal formation and growth at childhood and is required for proper skeleton function and musculoskleletal repair in adults. A variety of orthopedic pathologies are caused by or associated with impairment or dysregulation of systemic or local endochondral ossification. Fractures in the growth-plate (GP) can attenuate the endochondral ossification progress, resulting in stunted bone growth whereas diaphyseal fractures in long bones can provoke excessive bone growth, presumably due to regional activation of the GP function. In either case, the serious imbalance in bone growth inevitably leads to progressive deformity and significant physical problems. Surgery currently is the only treatment methodology.

Heterotopic ossification (HO) is a pathological condition driven by ectopic induction of abnormal endochondral ossification. Therapeutic management of the long bone growth and genetic HO requires a long-term, site-specific treatment. Currently there is no drug that has shown adequate therapeutic effectiveness with local administration. Systemic administration of high doses of RARγ agonists cause early closure of GP and inhibits consequent bone growth while systemic administration of RARγ antagonists enhances cartilage growth and delays maturation of GP chondrocytes. This systemic administration, however, does not allow for specific targeting of a single bone or a single area, and can be responsible for additional systemic effects, which may be undesirable. This invention therefore provides a formula and method that can treat conditions related to dysregulation of or abnormal endochondrial ossification specifically and locally.

This invention, in providing a clinically viable (non-surgical) treatment for post-traumatic HO and for FOP, focused on retinoic acid signaling to develop pharmacologically selective drugs for these pathologies. Retinoic acid, the active form of vitamin A, plays a key role in numerous biological processes, including skeletogenesis and myogenesis. Its action is mediated by various combinations of nuclear hormone receptors that act primarily as a transcription factor: heterodimers of retinoic acid receptor (RAR) with retinoic acid receptor X (RXR) translocate into the nuclei, bind to specific DNA sequences featuring a retinoic acid responsive element (RARE) and regulate target gene expression (genomic action).

In addition, the RARs modulate other signaling pathways through protein-protein interaction, phosphorylation, and by limiting the availability of cofactors for other transcription factors. RAR signaling is governed by the specific expression pattern of RAR isoforms and in addition depends on the availability of the intracellular active ligands. One a particular type of nuclear retinoid receptor, RARγ, plays a major role in longitudinal bone growth by controlling the rate of transition from cartilage to bone. Specifically, pharmacological activation of RARγ causes early closure of GP and inhibits further bone growth while inactivation of RARγ delays maturation of GP chondrocytes.

Because RARγ is a dominant RAR isoform in cartilage and retinoic acid is a strong inhibitor of chondrogenesis. Selective activation of RARγ was tested for its effects on preventing or reducing HO by inhibiting chondrogenesis, an initial step of HO. In addition, tests revealed that selective agonists for RARγ strongly inhibit both post-traumatic and congenital heterotopic ossification (HO) with fewer side effects compared to either retinoic acid or pan-agonists for RARs. Systemic administration of high doses of RARγ agonists causes early closure of GP and inhibits further bone growth, whereas RARγ inactivation delays maturation of GP chondrocytes. Therefore, pharmacological activation or blockade of RARγ signaling can be a therapeutic modality for controlling bone growth by modulating endochondral ossification in GP.

RARγ is responsible for retinoid-mediated inhibition of chondrogenesis and pharmacological activation of RARγ effectively blocks heterotopic ossification (HO), a pathology in which excess endochondral bone forms and accumulates within muscle and connective tissues. Oral administration of selective RARγ agonists strongly inhibits HO induced by subcutaneous or intramuscular transplantation of rhBMP-2-containing Matrigel™ or collagen sponge. Furthermore, the RARγ agonists reduced HO in mice harboring an ALK2 mutations seen in fibrodysplasia ossificans progressiva (FOP) patients. Given that the RARγ agonists reduce endochondral bone formation, it follows that RARγ antagonists should do the opposite and stimulate endochondral bone formation. Therefore, this can provide a new tool to stimulate bone formation at targeted sites.

Promoting bone defect repair can have benefits in many current clinical settings such as spinal fusion surgery, fracture repair and bone distraction. Although bone morphogenetic proteins (BMPs) have been used systemically for bone regeneration, a large dose of BMP can cause complications such as excess or heterotropic ossification, enhancement of local inflammation, loosening of the fixative device due to bone resorption, and even an increase in cancer risk. Clearly there is a need to develop a better strategy for bone regeneration in a repair scenario.

B. Nanoparticles

The pharmacological efficacy of systemic drugs is dependent on their distribution throughout the body as well as the elimination route and kinetics. More effective and safe drug action can be achieved by concentrating the active compound at the target site while reducing its systemic distribution. This invention relates to the strategy of drug incorporation into submicroscopic biodegradable drug carriers (nanocarriers) for controlling the pharmacokinetics of therapeutic substances at a specific site. Nanocarriers are designed to provide a means for delivering therapeutic agents to their site of action while minimizing off-target effects on healthy tissues and protecting the drug itself from premature decomposition and inactivation.

Entrapment in biodegradable polymer-based particles can help address delivery issues for compounds that are poorly soluble in or incompatible with traditional pharmaceutical vehicles and stabilize chemically labile agents in the biological milieu. Adjustments in the particle manufacturing process it make possible to achieve release kinetics optimal for the pharmacological action of a particular therapeutic compound. Furthermore, the small size of biodegradable nanocarriers relative to larger-sized microparticles renders them more efficacious and safer. Their other advantages include minimal inflammatory reaction in tissues, enhanced interaction with tissue components, and the option of delivering drugs intracellularly where necessary for a particular therapeutic application.

RARγ drug-loaded nanoparticle (NP) formulations provide controlled release of a potent RARγ agonist for local administration with long retention in muscle and bone. These formulations release biologically active RARγ agonists or antagonists that are shown here to affect both ectopic bone formation and longitudinal growth of the targeted bone. RAR specific retinoids formulated in these biodegradable nanoparticles for site-specific delivery to the musculoskeletal tissues can control longitudinal growth of the targeted bone and inhibit heterotropic ossification (HO). This provides a new nanocarrier-based drug therapy for conditions such as HO and for correcting bone growth imbalance where endochondrial ossification has become dysregulated, which meets the need for new, safer and more effective, orthopedic treatment strategies.

The nanoparticles are spherical in shape, with a uniform size distribution as determined by photon correlation spectroscopy. The encapsulated drug is uniformly dispersed throughout the nanoparticle matrix. The drug:polymer weight ratio can be varied to modify the drug loading and release kinetics from 80 mg:200 mg to 0.5 mg:200 mg. The ratio of 15 mg:200 mg used in Example 1, below was found to provide an excellent entrapment yield (≥50%) in combination with good colloidal stability, narrow size distribution and capacity for lyophilization. Blank (drug-free) nanoparticles can be prepared as above, without adding the drug to the organic phase prior to the emulsification step. Polylactide is the nanoparticle-forming polymer (i.e. constitutes the polymeric matrix of the nanoparticle). Albumin acts as a colloidal stabilizer, providing electrosterical stabilization and preventing aggregation of the nanoparticle dispersion.

Stable fluorescent labeling of the nanoparticles is achieved by covalent modification of the matrix-forming polymer with a BODIPY dye that exhibits environment-insensitive fluorescence, high extinction and quantum yields, and narrow excitation and emission unachievable with the older generation probes. Fluorescently labeled nanoparticles for cell uptake and biodistribution studies were prepared as above, with 4 mg of plain polylactide (PLA) replaced with an equivalent amount of PLA covalently modified with 4,4-difluoro-4-bora-3a,4a-diaza-s-indacene (boron-dipyrromethene ($BODIPY_{558/568}$). These fluorescently labeled NPs were retained at the delivery site over 2 weeks, demonstrating the ability to exert a long-term effect when loaded with drug. See Example 9 for more information on production of these NPs.

The release rate of the investigated retinoid compounds from nanoparticles is a key to controlling their biodistribution, achieving sustained local effects in the targeted tissue and minimizing dissemination from the site of delivery. Thus, achieving extended but controllable release is important for optimizing the efficacy and safety profile of any therapeutic strategy. Reducing the surface area-to-volume ratio by increasing the size of the nanocarriers or decreasing drug diffusivity through the particle matrix by employing a higher molecular weight polymer can both provide convenient, readily applicable tools for adjusting the release kinetics, stabilizing the chemically labile retinoid compounds and extending their local presence in the pharmacologically active form at the diseased site, thus taking full advantage of site-specificity and controlled drug release offered by nanocarrier-mediated delivery.

RARγ agonist-loaded NPs strongly inhibited matrix production over a week in cultured chondrocytes, confirming sustained bioactivity of the encapsulated drug. Further, locally delivered drug-loaded NPs inhibited ectopic bone formation and significantly reduced longitudinal growth of the applied long bone without affecting other bones. See below.

C. RAR Drugs

Treatment with selective RARγ antagonists stimulated cartilage matrix production and inhibited chondrocyte hypertrophy. These observations can explain the mechanism of stunted bone growth caused by hyper-vitaminosis A. Thus, RARγ agonists and antagonists can be used to manipulate growth plate function and thereby bone growth. With site-specific delivery, RARγ agonists can disturb longitudinal growth of the targeted bone without systemic effects on the skeleton as a whole or on other bones nearby. Likewise, locally administered RARγ antagonists can inhibit hypertrophy of chondrocytes and prevent premature closure of GP resulting in extension of bone length with the same lack of systemic effects.

Figures 18A, 18B, 18C:
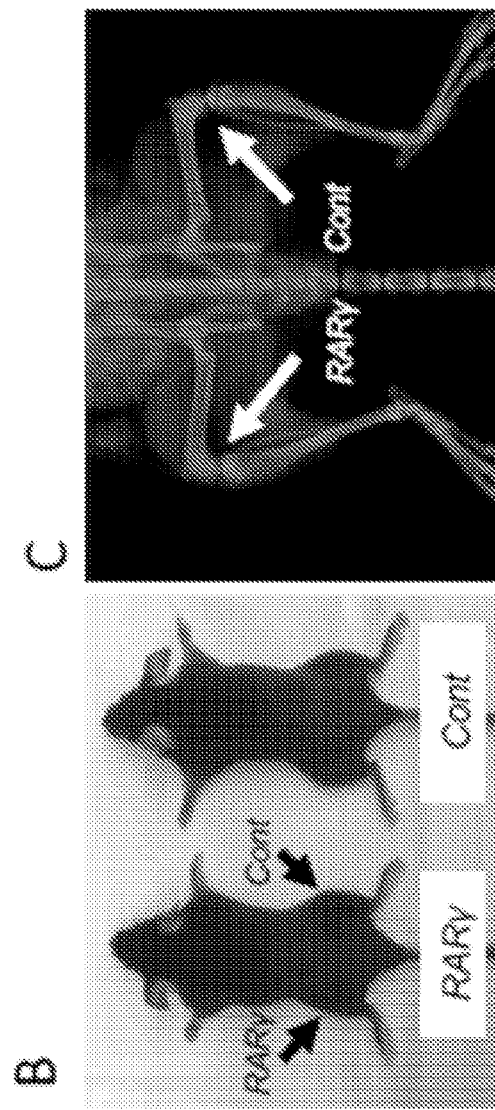
FIG. 18A is a schematic drawing that illustrates drug injection sites near the growth plate of proximal tibia.
FIG. 18B shows whole body images of NP-injected (left) and non-treated (right) mice.
FIG. 18C is a soft X-ray image of mouse hind limbs that received NRX-NP (left) or blank/unloaded NP (right).
Figure 18E:
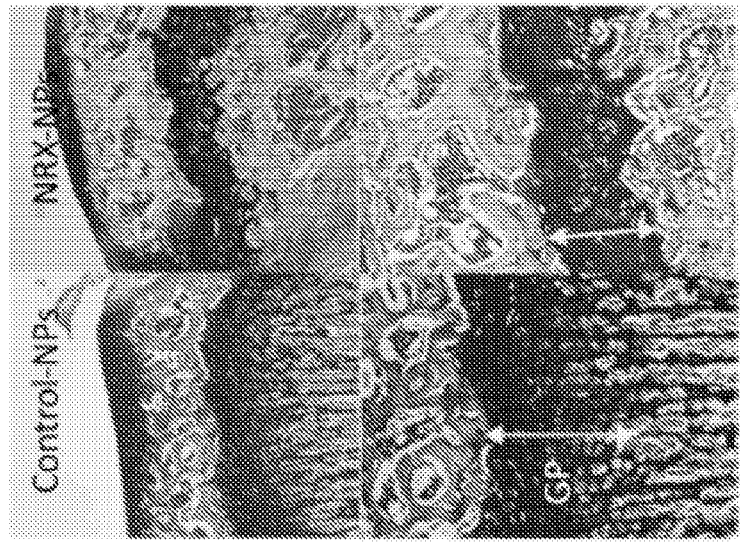
FIG. 18E is a set of macro images of the epiphyseal regions of control-NP- and NRX-NP-treated bones.
Figure 18D:
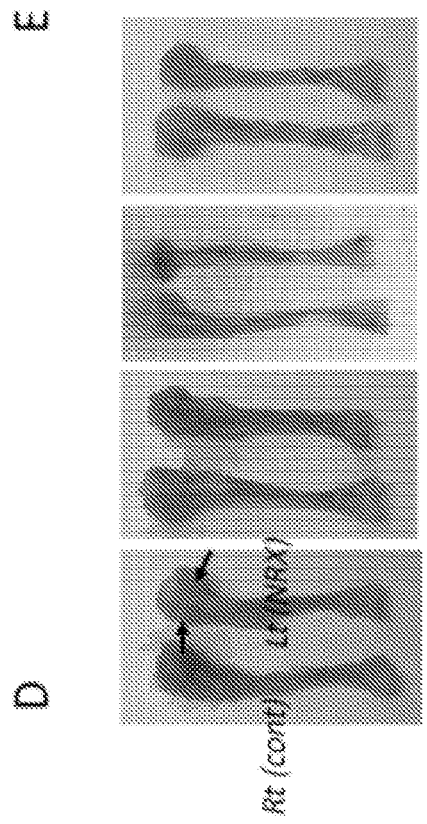
FIG. 18D is a set of macro images of control (right) and NRX-NP-treated bones.

The bone growth model testing demonstrated usefulness of RARγ agonist-NPs for specifically restricting longitudinal growth of long bones. Local administration of NRX204647-NP caused growth plate (GP) closure within 8 days, therefore a lower dose of RARγ agonist-NP can be expected also to restrict bone growth in a dose-dependent manner. When a NP suspension carrying 4.5 μg NRX20467 was injected adjacent to the proximal GP of the left tibia in 2-week old mice (the right tibia received PBS), after 2 weeks there was no obvious difference in gross appearance between the treated (left) and non-treated (right) mice (FIG. 18B). X-ray image analysis, however, detected GP closure of the left tibia (arrow, FIG. 18C) and the isolated bones showed an apparent difference in the length between NRX- and PBS-treated bones (FIG. 18D). The results demonstrated that NRX204647-loaded NPs specifically inhibited bone growth at the targeted bone without affecting growth of other bones.

Figures 4A, 4B:
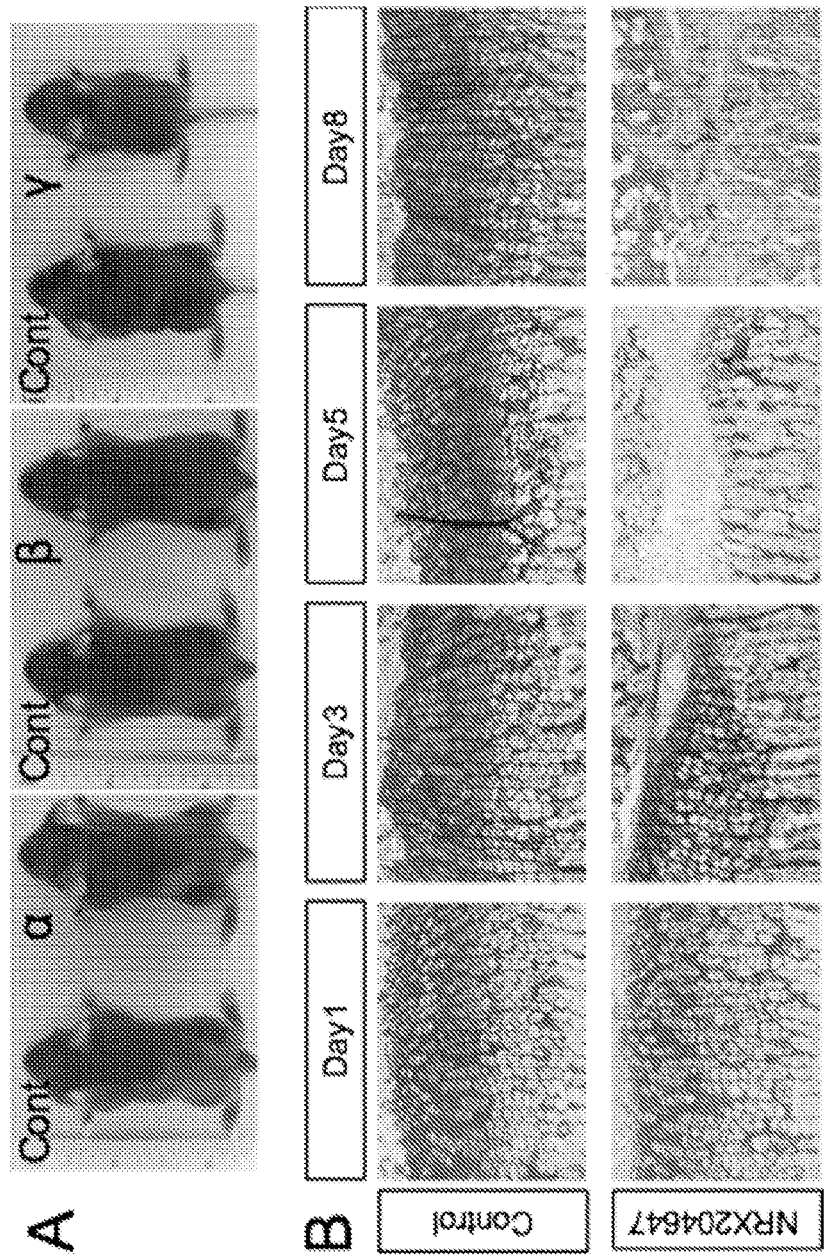
FIG. 4A is a series of photographs showing the effect of RAR agonist treatment on body length, including RARα, RARβ and RARγ.
FIG. 4B is a series of photographs of histology sections of tibial growth-plate in control and NRX204647 (agonist)-treated mice at the indicated time points.

This is in sharp contrast with mice given NRX204647 by oral gavage (systemic administration) which became proportionally smaller in body size than control mice (FIG. 4A). The findings clearly indicate that NPs-based drug delivery is effective at controlling bone growth at a desired site. These data indicated that retinoid drug-loaded nanoparticles can be applied to specific sites within musculoskeletal tissues to control longitudinal growth of a targeted bone, inhibiting HO.

To restrict longitudinal bone growth proportional manner, the NP should be administered in an even manner around the bone or into the bone marrow space, which allows the released active retinoids to diffuse more evenly in the entire marrow space. Locally administered RARγ agonist-NP administered to only one side of the bone affects the GP unevenly due to uneven concentrations of active retinoids and can be used to restrict growth more on the side of the injection. This allows one to target only a part of the GP and guide the growing direction of the target bone to correct malalignment of joints. This is useful in correcting conditions such as knock knees or bow-leggedness by adjusting the angle of the knee joint or the bones of the leg.

RARγ antagonist-loaded NP have the opposite effects to those described here for RARγ agonists. Primary targets pf RARγ antagonists are chondro-progenitor cells and chondrocytes, but not osteoblasts (FIG. 7). Without wishing to be bound by theory, inhibition of RARγ action by retinoid antagonists therefore operate by stimulating chondrogenic differentiation of mesenchymal cells and increasing matrix production in chondrocytes, resulting in increases in cartilage volume and in turn, stimulation of increased bone formation.

RARγ antagonist NPs of embodiments of the invention are potent stimulators of cartilage growth which inhibit cartilage-to-bone transition in endochondral ossification processes. Therefore, RARγ-antagonist NPs can stimulate longitudinal bone growth by inhibiting chondrocyte maturation and slowing down the replacement of growth plate cartilage with bone, delaying closure of the growth plate. Systemic administration of an RARγ antagonist markedly increased cartilage formation, leading to more bone formation. Therefore, the RARγ antagonist-loaded NP are useful to promote longitudinal bone growth.

Ectopic endochondral ossification was induced by subcutaneous implantation of bone morphogenetic protein BMP-2 containing Matrigel™ in wild type mice. Ectopic bone volume/total volume (BV/TV) was significantly increased by treatment with three different types of RARγ antagonists. The stimulatory effect of RARγ antagonists was not found in RARγ null mice. Histomorphometric analysis revealed that stimulation of ectopic cartilage formation preceded an increase in bone formation under treatment with RARγ antagonists. Presence of phosphorylated Smad1/5/8 was more evident in the bone defect in RARγ null mice and the BMP-Matrigel™ implant treated with RARγ antagonists compared to the wild type bone defect and the vehicle-treated implant, respectively. Stimulation of Smad 1/5/8-BMP signaling by RARγ antagonists also was found in primary mouse chondrocyte or ATDC5 cell cultures. Interference with RARγ function stimulates bone formation and does so at least in part by stimulation of the canonical BMP signaling pathway.

Systemic administration of RARγ antagonists enhances BMP signaling and synergistically induces a large amount of bone formation. RARγ antagonist NP can be injected locally together with BMP, BMP and bone inducing grafting materials, or BMP/scaffold/skeletal progenitor cells to promote repair of bone defects, fracture healing and spinal fusions surgery. An RARγ antagonist in the combination reduces the required dose of BMP for the procedure, leading to the reduction of treatment cost and the risk of BMP-induced complications.

In vitro studies showed that RARγ physically interacts with the MH2 domain of Smad3 and down-regulates Smad3/4-dependent transcription in the presence of RARγ agonists, while Smad3/4-dependent transcription activity was markedly increased by RAR pan-antagonist treatment. The MH2 domain is used for protein-protein interactions, including hetero-trimerization of Smads, and is highly conserved, especially among the R-Smad proteins. Thus, RARγ can directly interact with Smad1/5/8 proteins and modulate their function. On the other hand, RARγ is also known to interact with Src, a non-receptor tyrosine kinase, and ligand-bound RARγ enhances Src kinase activity. Other reports have demonstrated that Src interacts with the C-terminal domain of BMP type II receptors, and suggest that RARγ indirectly interacts with BMP receptor and could modulate BMP receptor function. RARγ also may regulate the transcription of genes related to BMP signaling.

The repair of tibial bone defects is accelerated in RARγ-null mice compared to control mice and that pharmacological inhibition of RARγ function by selective antagonists stimulates ectopic endochondral bone formation. In both experimental systems, local BMP signaling is enhanced as determined by marked increases in pSmad1/5/8 levels. This finding is in line with in vitro observations suggesting that treatment with RARγ antagonists stimulates BMP signaling rapidly and significantly. Together with studies showing that pharmacological activation of RARγ function blocks ectopic endochondral ossification in mice and inhibits canonical BMP signaling, the results presented here indicate that RARγ is an actor in the regulation of endochondral ossification and can represent a therapeutic method to manipulate and enhance bone formation in various pathological skeletal conditions.

The studies presented here also show that an RARγ agonist showed significant reduction of HO in both acquired and genetic HO animal models primarily by inhibiting cartilage formation, although the complete suppression of genetic HO required a large dose of the systemically administered drug. Such a treatment regimen caused inhibition of bone growth by early closure of GP. In contrast, RARγ antagonists enhanced cartilage growth and delayed maturation of GP chondrocytes. A minimally invasive local drug delivery system to correct imbalance of bone growth, a condition that continues to pose an unmet need for effective and safe treatment options, was developed.

Repeated injections may trigger injury-induced HO and can be counteracted with the pharmacological action of RARγ agonists, so it is better to avoid an unnecessarily larger number of injections where possible. Therefore, an additional approach to controlling biodisposition, stability, and release rate of the particle cargo and potentially maintaining an active concentration of retinoid in the target tissue over a longer time period and reducing the number of administrations required for sustained therapeutic action, is to form in situ activatable prodrugs that are cleaved to regenerate the active molecule at a predictable rate. Thus, prodrug-loaded NPs can release active compound consistently for much longer period and so can ameliorate any problems caused by the frequency of injection.

In order to produce an in situ activatable, reversibly hydrophobized prodrug derivatives of a RARγ agonist, a pro-drug can be delivered in a nanoparticle formulation. Retinoids discussed in the present project are amphiphilic compounds possessing uncapped carboxylic groups required for their effect on the retinoid receptor. However, the ionizable carboxylic group promotes the partitioning of the compound from the particle to the surrounding aqueous medium. Therefore, capping this chemical function in a reversible manner with a suitable non-toxic molecule to make a significantly more hydrophobic derivative (5-fold for MM 11253 and 15-fold for palovarotene), if modified with acetaminophen as discussed here) can be achieved. The compound would be activatable upon release can increase the stability of the particle-cargo association and help achieve a more lasting and highly localized therapeutic effect. Such constructs are in essence mutual prodrugs or co-drugs, as they regenerate in one step the retinoid compound and acetaminophen, a biologically active "helper" agent, which can play an important supporting role in therapy.

Prodrugs of this type can include a palovarotene pro-drug, which can be synthesized by direct coupling of palovarotene with acetaminophen in a mixture of dichloromethane ($CH_2Cl_2$) and N-methyl-2-pyrrolidone (NMP) using 1-ethyl-3-(3'-dimethylaminopropyl) carbodiimide hydrochloride (EDC) as a coupling reagent and 4-dimethylaminopyridine tosylate (DPTS) as a catalyst. The crude product can be purified by flash chromatography (silica-gel, chloroform-acetonitrile, 100:0 to 10:1). 1H NMR (400 MHz, CDCl3) and TLC (silica-gel plate, chloroform-acetonitrile, 7:3) can be applied to confirm the structure and the purity of compound according to known methods.

The pro-drugs above have a significantly higher organophilicity than that of the parent drug, which can increase the stability of the particle-cargo association. Upon release, the pro-drug generates active drug through hydrolytic cleavage, at a rate characteristic of phenolic esters. This activation step adds another layer of control in drug release. The released acetaminophen may be beneficial as an analgesic locally, however the amount of acetaminophen delivered in this manner is far less than its effective systemic dose.

A prodrug of the RARγ antagonist, MM 11253 with acetaminophen was prepared by direct coupling of the components in a mixture of dichloromethane ($CH_2Cl_2$) and N-methyl-2-pyrrolidone (NMP) using 1-ethyl-3-(3'-dimethylaminopropyl)carbodiimide hydrochloride (EDC) as a coupling reagent and 4-dimethylaminopyridine tosylate (DPTS) as a catalyst (Scheme 1). Details are provided below in Example 2.

RARγ modifying agents include but are not limited to an RARγ agonist, an RARγ partial agonist, an RARγ antagonist, an RARγ blocker, an RARγ binder, and the like. These RARγ modifying agents are pharmaceutical compounds and can be used in the form of pharmaceutically acceptable salts, acids, hydrates, and solvates, or as a base. These compounds can exist in amorphous form or in any crystalline form. Preferably, the pharmaceutical compositions comprise a therapeutically effective amount.

Any pharmaceutically acceptable salt can be used, as may be convenient. Generally, these salts are derived from pharmaceutically and biologically acceptable inorganic or organic acids and bases or metals. Examples of such salts include, but are not limited to: acetate, adipate, alginate, ammonium, aspartate, benzoate, benzenesulfonate (besylate), bicarbonate, bisulfate, butyrate, citrate, camphorate, camphorsulfonate, carbonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, magnesium, maleate, malonate, methanesulfonate (mesylate), 2-naphthalenesulfonate, nicotinate, nitrate, oxalate, palmoate, pectinate, persulfate, 3-phenylpropionate, phosphate, picrate, pivalate, potassium, propionate, salicylate, sodium, succinate, sulfate, tartrate, thiocyanate, toluenesulfonate (tosylate) and undecanoate salts.

According to the invention, the RXRγ modifiers are entrapped in the nanoparticles described herein, and preferably these particles are contained in a pharmaceutically acceptable carrier, excipient, or vehicle in at least some embodiments. Suitable carriers depend on the route of administration contemplated for the pharmaceutical composition. Such routes can be any route which the practitioner deems to be most effective or convenient using considerations such as the patient, the patient's general condition, and the specific condition to be treated. For example, preferred routes of administration can include, but are not limited to: direct injection to the area to be treated, such as bone, cartilage, tumor, or the area near to or surrounding these, or wherever needed. Alternatively, routes of administration can include but are not limited to intravenous, intraarterial, intrathecal, subcutaneous, intraperitoneal, or local injection, and the like, to be determined by the practitioner. Therefore, preferred dosage forms which the pharmaceutical composition can take will include, but are not limited to: solutions, suspensions, emulsions, dispersions, powders for dilution, oils, gels, and packaging therefor (e.g., ampoules, bottles, pre-filled syringes, and the like).

The carrier or vehicle can contain one or more ingredient such as solvents (e.g. water, alcohol, polyol, and the like), salts (e.g., sodium, potassium, calcium, chloride, phosphate, lactate, and the like), oils, buffers (e.g. acetate, citrate, bicarbonate, and the like), pH adjusters (acid, base), emulsifiers, suspending agents, wetting agents and surfactants, dispersants, antibacterial agents, antioxidants, chelating agents, (e.g., EDTA and the like), and buffers (e.g., acetate, citrate, phosphate, carbonate and the like).

D. Methods and Applications

At present, surgery is the only means to correct significant imbalance of bone length or malalignment of the bones. Systemic drugs with undesirable side effects are used for conditions related to EO, but no feasible treatment is available for site-specific, local treatment of EO. Local control of endochondral ossification by alteration of RARγ signaling provides the basis for pharmacotherapeutic correction of the imbalance or dysregulation of long bone growth. In addition, through enabling spatial and temporal pharmacological targeting of the endochondral ossification process in GP and HO, nanoparticle-based delivery according to embodiments of the invention can offer an effective and safe new therapeutic modality in the therapeutic context of HO and FOP.

Synthetic retinoids are small in size (about 400 MW), relatively stable and easy to administer. RARγ antagonists and agonists now are shown to be easy-to-use and versatile modulators of endochondrial bone formation useful in various clinical settings, where localized and sustained inhibition of bone growth, stimulation of bone growth, correction of bone growth imbalances, assisted repair of fractures and other trauma to bone, joint alignment, tumors, and acquired or genetic heterotropic ossification.

For example, large bone defects caused by trauma, surgery, or any cause currently are treated by local application of growth factors, such as BMP2 and BMP7, scaffolds or bone grafts, adult stem/progenitor cells or a combination of these techniques. RARγ antagonists in NP formulations according to the invention can be applied directly to a bone defect by incorporation into the scaffolds, for example. Since the RARγ antagonists enhance BMP signaling only in RARγ-responsive cells, it can effectively promote endochondral ossification and reduce the amount of recombinant BMPs needed to repair a bone defect. Such a reduction would not only reduce cost, but may decrease the risk of adverse effects by the BMPs such as local inflammation, tissue swelling, osteolysis, and the like, by reducing the amount of BMP needed.

For treatments using BMP, RARγ antagonists can be administered to the patient at the time of the BMP application or administered later when locally administered BMP does not induce enough bone formation. RARγ agonist-loaded NP also are useful to reduce side-effect caused by excessive host response to BMP. Any time after application of BMP for bone repair, RARγ agonist NP can be locally injected as soon as the clinician finds a sign of inflammation or excess bone formation by imaging. If the inflammation is wide-spread and/or swelling airway is evident (an indicator that requires immediate attention), RARγ agonist can be administered orally. For either agonist or antagonist, the drug dose preferably is 10 μg-10 mg, more preferably 20 μg-5 mg, and most preferably 50 μg-1 mg, (local injection of Retinoid-loaded NP), or 5 mg-20 mg per 50 kg body weight/day, more preferably 7.5 mg-15 mg per 50 kg body weight/day, and most preferably 10 mg-20 mg per 50 kg body weight/day (oral administration). The treatment frequency of retinoid-loaded NPs preferably is every 1-4 weeks by local injection. When administering orally, administration preferably is daily administration.

Spinal fusion surgery is an example where RARγ antagonists can be useful. Since the Food and Drug Administration first approved the use of rhBMP-2 for fusion of lumbar spine in mature patients in 2002, BMPs have been widely used in connection with spinal fusion surgeries. Although the BMPs are beneficial for spinal fusion, they can cause complications such as heterotopic ossification, neuropathy and compression of airway in some patients. These adverse effects are difficult to predict due to variability in patient-to-patient BMP responses. Thus, using RARγ antagonists can reduce the risk of these complications by reducing the BMP amounts needed for spinal fusion surgery. NP drug formulations of this invention are contemplated for use in any of these applications. In lumber spinal fusion, about 4-40 mg of BMP2 is used. Since selective RARγ antagonist increases ectopic bone formation by BMP2 roughly 10-fold, the dose for combination therapy preferably is about 0.4-4 mg BMP2 and about 10 μg-1 mg of RARγ antagonist-NP. When efficacy of previously applied BMP is not strong enough, 10 μg-1 mg of RARγ antagonist-NP can be applied to enhance BMP action. The treatment frequency of RARγ antagonist NP will be 1-3 times every 1-4 weeks depending on the patient's response.

The administration of RARγ agonists according to embodiments of the invention also is useful as a treatment for osteochondroma, a cartilage tumor. Local administration to the tumor site using methods according to the invention can increase the amount of drug at the tumor site while reducing unpleasant systemic effects. For patients who suffer from sporadic or multiple osteochondromas, the RARγ agonists-loaded NP can be locally administered to the vicinity of tumors by injection. The local administration can be guided by fluoroscopy aiming at the tumors. The frequency will be 1-3 times weekly for 1-3 months. The dose preferably is 10 μg-3 mg of RARγ agonists.

Pediatric long bone fractures require careful follow-up because fractures in the growth-plate (GP) or diaphysis could lead either inhibition or acceleration of bone growth, causing imbalance and skeletal deformity. Chronic exposure of excess vitamin A or retinoic acid (RA) also causes early closure of the GP, leading to shortened bone. Either of these conditions can result in progressive growth imbalance, deformity and/or other significant physical or orthopedic problems. The compositions and methods of certain embodiments of the invention can be used to correct these conditions by selectively stimulating or inhibiting bone growth at a particular location in the skeleton. This includes correcting imbalances of bone length and/or alignment. One advantage of drug-based manipulation of targeted bone growth is that the drug can be used to correct previously untreated minor skeletal deformity. Fine adjustment of the targeted bone growth should be beneficial to reduce arthritis and other complications.

By applying RARγ agonist-NP to multiple sites around a GP, longitudinal growth of the targeted bone is proportionately restricted. Proportional restriction of bone growth also can be achieved by intra-bone marrow injection of RARγ agonist NP. By applying RARγ agonist-NP to only one side of the GP, the part of the GP near the injection site undergoes early closure. As a result, the joint surface will be tilted towards the drug injection side. Such treatment is useful to correct bone alignment in a joint. This can be used to prevent worsening of bow-leggedness and knock knees. Depending on the severity of imbalanced bone length/alignment, and the size of bone (growth-plate), drug dose may vary. Typically, for growth-restriction, 10 μg-1 mg of RARγ agonist NP is injected per site. For peri-growth-plate or intragrowth-plate injection, the drug can be injected in 2-4 sites per bone. When the drug is injected into bone marrow space, preferably 10-3 mg of RARγ-NP is injected. The preferred frequency of local administration is once every 1-4 weeks. Guided drug injection by fluoroscopy is optional. Flouroscopy allows physicians to locate the needle position and growth-plate.

Embodiments of the invention also can be used to exert therapeutic control over bone growth to prevent genetic or acquired HO, including FOP, by providing a long-lasting effect while being highly site-specific, in order to minimize drug dissemination and unwanted systemic effects. Here, one-time application of RARγ agonist loaded NP effectively suppressed HO for a prolonged time period. By locally injecting the RARγ-NP or in combination with systemic administration of palovarotene (Phase III RARγ agonist), HO can be blocked almost completely. For such application, 10 μg-10 mg RARγ agonist-NP (NRX204647 or palovarotene or CD1530 or any RARγ agonist) preferably is injected directly into or around the affected site. Treatment frequency generally is every 1-4 weeks depending on the size of affected region. In the case where the HO forming region is wide-spread, NPs with smaller diameter (100-200 nM) are preferred to facilitate diffusion of the locally applied NPs.

Figure 10:
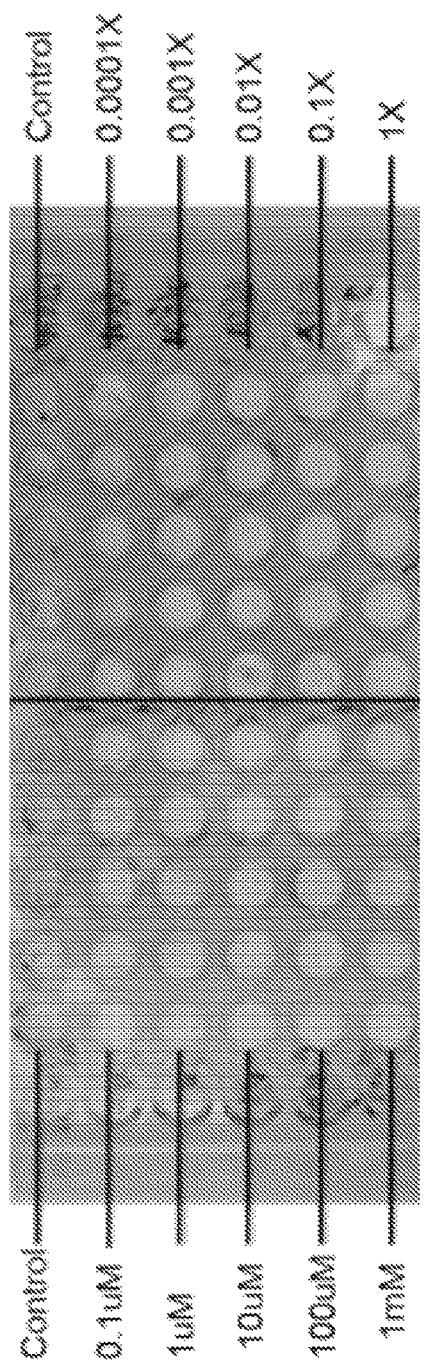
FIG. 10 is a photograph of a plate showing the bioactivity of NRX204647 solution (left) and NRX204647-loaded nanoparticles (right).

NRX204647-loaded NPs exhibit appreciable bioactivities and sustained release of the loaded drug. NPs can be formulated to hold any appropriate RARγ agonist, however, for example, palovarotene, or any appropriate RARγ antagonist, for example MM11253 and 7a. Palovarotene is currently being evaluated in a phase III clinical trial for the prevention for HO in FOP patients. Though the potency (EC50) of palovarotene is inferior to that of NRX204647, its safety and pharmacokinetics have already been investigated, so this drug is contemplated. The RARγ antagonists CD2665, MM11253, 7a, and 7c have proven biological activities in an ectopic bone formation model. See FIG. 10, and FIG. 26 (Example 23).

The application of targeted drug delivery offers great potential for improving efficacy and minimizing side effects to non-target tissues. Targeted delivery systems can be instrumental for delivering drugs to their site of action, while protecting labile compounds from premature degradation, increasing bioavailability at the site where action is desired, limiting peripheral dissemination, and addressing solubility issues.

As discussed above, control and adjustment of specific long bone growth dysregulation requires achieving a highly localized and sustained therapeutic effect. Today, surgical resection combined with systemically administered anti-inflammatory drugs is the primary treatment modality for acquired HO. Treatment options for FOP are further limited. Because the surgical procedure itself can induce additional HO formation, systemic drug therapy aimed at reducing HO progression and related symptoms is the sole choice. Oral administration of a selective RARγ agonist, palovarotene, effectively reduces HO in FOP model mice. See FIG. 1. Recently released top-line results of an ongoing Phase II trial for the treatment of FOP suggest that systemic palovarotene is effective at reducing HO and pain associated with FOP, reducing HO in the patients up to 70%. However, despite the significant reduction in HO with this treatment regimen, systemic administration of the RARγ agonist fails to completely prevent the disease. Enhancing efficacy by increasing the systemic drug dosage may not be possible without causing strong and even toxic off-target effects. Thus, the inventive methods of treatment here increase the activity at the target site without inducing unwanted systemic effects using biodegradable nanoparticle (NP) formulations impregnated with a potent RARγ agonist capable of targeting specific areas of bone.

E. Summary

Because the expression level of RARγ is much higher in chondrocytes compared to other cell types in bone, administered RARγ agonists/antagonists preferentially act on chondrocytes in GP with minimal effects on non-target cells. Furthermore, the site-specific pharmacological therapy reduces side effects in non-skeletal tissues and enhances accessibility and effectiveness within specific affected sites.

The findings discussed here indicate that RARγ agonists/antagonists are agents for pharmacotherapeutic treatment of abnormal or dysregulated bone growth. A poly(D,L-lactide) (PLA)-based nanoparticle (NP) formulation was designed that has confirmed retention and sustained release of a potent biologically active RARγ agonist in vitro. A fluorescence-labeled NP was injected into several different mouse tissues; stable local retention of the injected NPs for a prolonged time period was confirmed. RARγ agonist-loaded NP were injected into the vicinity of the growth-plates of the tibia of growing mice, and were found to suppress longitudinal growth of the targeted bone without affecting other bones. RARγ antagonists were found to increase cartilage and bone growth. An RARγ agonist-loaded NP-based drug therapy can replace toxic systemic therapies and invasive growth-restriction surgeries for conditions involving dysregulation of endochondrial ossification.

5. Examples

This invention is not limited to the particular processes, compositions, or methodologies described, as these may vary. The terminology used in the description is for the purpose of describing the particular versions or embodiments only, and is not intended to limit the scope of the present invention which will be limited only by the appended claims. Unless defined otherwise, all technical and scientific terms used herein have the same meanings as commonly understood by one of ordinary skill in the art. Although any methods and materials similar or equivalent to those described herein can be used in the practice or testing of embodiments of the present invention, the preferred methods, devices, and materials are now described. All publications mentioned herein, are incorporated by reference in their entirety. Nothing herein is to be construed as an admission that the invention is not entitled to antedate such disclosure by virtue of prior invention.

Example 1. Materials and Methods

A. Nanoparticle Production

An aqueous dispersion of nanoparticles (NP) was prepared using a modification of the emulsification-solvent evaporation method. Fifteen mg of the drug were first dissolved in a mixture of 1 mL ethanol and 7 mL chloroform, followed by 200 mg of poly(D,L-lactide) (MW=35 kDa, Mn=19 kDa). The organic solution was emulsified by sonication on ice in 10 mL of a 0.2 µm filter-sterilized aqueous phase consisting of 100 mg of human serum albumin dissolved in deionized water. The obtained emulsion was transferred into a round-bottom evaporation flask, and the organic solvent was removed using a rotary evaporator at 30° C. under pressure gradually reduced from 200 to 40 mbar. Following the solvent evaporation step, human serum albumin and glucose (200 mg and 400 mg, respectively) were dissolved in the particle suspension. The suspension was sequentially filtered through a 1.0-µL glass filter unit, then through a 5.0 µm sterile filter into a presterilized glass vial and lyophilized. Lyophilized nanoparticles were kept at −80° C. and resuspended in deionized, sterile water before use.

The nanoparticles are spherical in shape, with a uniform size distribution as determined by photon correlation spectroscopy. The encapsulated drug is uniformly dispersed throughout the nanoparticle matrix. The drug:polymer weight ratio can be varied to modify the drug loading and release kinetics from 80 mg:200 mg to 0.5 mg:200 mg. The ratio of 15 mg:200 mg used in the present example was found to provide an excellent entrapment yield (≥50%) in combination with good colloidal stability, narrow size distribution and capacity for lyophilization. Blank (drug-free) nanoparticles can be prepared as above, without adding the drug to the organic phase prior to the emulsification step.

Fluorescently labeled NP were obtained using the same methods. In brief, 4 mg of PLA-BODIPY$_{558/568}$, were mixed with 196 mg unlabeled PLA and a retinoid drug dissolved in a mixture of ethanol/chloroform (1 mL:7 mL). The organic phase was emulsified by sonication in an aqueous solution of human serum albumin, and the solvent removed under reduced pressure. NP then were collected, lyophilized, stored at −80° C., and reconstituted in deionized water before use.

The practitioner will be aware that the formulation can be adjusted to optimize a particular drug formulation or purpose by adjusting the following variables: drug to polymer and organic to aqueous phase ratios, albumin content, and the like. Chloroform used as the basis for the organic phase can be replaced with another water-immiscible or partially water-miscible solvent (e.g. dichloromethane or ethyl acetate). Albumin in the aqueous phase can be replaced with chemically different, natural or artificially made, stabilizers, such as Poloxamer polymers, polyvinylpyrrolidone or polyvinyl alcohol. Alternatively, by manufacturing similarly sized NPs with higher or lower molecular weight PLA (some examples include Mw/Mn 122/77 kDa; Mw/Mn=35/19 kDa, or Mw/Mn=11/4 kDa), drug partitioning can be decreased or increased. The release kinetics can be adjusted by replacing poly(D,L-lactide) with other biodegradable particle-forming polymers, include the more crystalline poly(L-lactide), poly(lactide-co-glycolide), poly(lactide)-b-poly(ethylene glycol), and/or poly(epsilon-caprolactone), as well as their mixtures. The particle size can be varied by including biocompatible, water-miscible solvents in the organic phase, such as acetone, acetonitrile, tetrahydrofuran, or by increasing the amount of ethanol. All NP formulations preferably are routinely characterized for stability, composition, and size distribution.

The drug loading of NP was determined spectrophotometrically against suitable calibration curves following two-step drug extraction in sec-butanol. Particle size measurements were performed by dynamic light scattering using a 90 Plus Particle Size Analyzer. An external sink method was applied for measuring drug release kinetics under sink conditions as follows: NP were diluted in PBS/2% bovine serum albumin and incubated with a water-immiscible acceptor medium (1-octanol and n-heptane, 1:1 v/v), and the released drug assayed spectrophotometrically in the acceptor medium samples at predetermined time-points.

B. Ectopic Bone Formation Model

The ectopic bone formation model is used as a preliminary test to determine whether and how the retinoid-NPs directly inhibit or stimulate endochondral ossification in a semi-quantitative manner. Ectopic bone formation was induced in mice according to known methods. See Shimono et al., J. Orthop. Res. 28(2):271-277, 2010. Briefly, recombinant human bone morphogenetic protein-2 (rhBMP-2; Gene Script™ Corp., Piscataway, NJ) was added to growth-factor reduced Matrigel™ (BD Bioscience™, Inc., Franklin Lakes, NJ) on ice to a final concentration of 4 g/mL. Two hundred fifty 250 µL, rhBMP-2-containing Matrigel™ was injected into the left and right subcutaneous abdominal region of 2-month-old CD-1 female mice. Ectopic tissue samples were harvested and subjected to µCT and histological analyses.

C. Tibia Defect Repair Model

Under anesthesia and analgesia, the surgical site was shaved using a sharp razor and a skin incision was made over the medial aspect of the tibia in two-month-old female RARγ null and wild type mice. To gain access to the tibia, the tibialis anterior muscle was divided carefully and avoiding damage to the tibial periosteum. A 1 mm-diameter hole was drilled in the midline, 5 mm below the tibia patellar tendon insertion of the tibia, using a 21-gauge needle and a dental carbide bur (size 6, Henry Schein™ Inc., Melville, NY) attached to a micromotor (RAM Products™ Inc., Bruinswick, NJ) with continuous irrigation with saline. The skin was closed with 6-0 nylon sutures. The mice were sacrificed at day 7 or day 14 and the tibias were processed for histological and µCT analysis. To assess bone formation activity, some mice received an intraperitoneal injection of 30 mg/kg calcein (C0875, Sigma-Aldrich) 24 hours before euthanasia.

D. Preparation and Administration of Retinoids

The RARγ agonists R667 (palovarotene, CAS410528-02-8) and NRX 204647 were synthesized by Atomax Chemicals (Shenzhen, China). The RARγ antagonists CD2665 (CAS 170355-78-9) and MM11253 (CAS345952-44-5) were purchased from Tocris Biosciences™ (Bristol, UK). RARγ antagonists 7a and 7c were synthesized by Atomax Chemicals (Shenzhen, China) according to methods provide in international patent application WO 2005/066115 A2. The concentrations of retinoid used for animal experiments were 1 mg/kg for NRX 204647 and 4 mg/kg for all others unless indicated. Stock solutions of retinoids in DMSO (Sigma-Aldrich, D2650) were stored at −30° C. under argon. Before administration, 30 µL aliquots of stock solution were mixed with 70 µL of corn oil for each dose, and administered to mice by oral gavage using a 20-gauge gavage needle. Vehicle control mice received 30 µl, DMSO plus 70 µL corn oil in the same manner.

E. Histological and Immunohistochemical Analyses

Tissue samples were fixed in 4% paraformaldehyde overnight at 4° C., decalcified in 10% EDTA (for calcified samples only), processed for paraffin embedding, and serially sectioned at 6 μm-thickness. Sections were stained with hematoxylin and eosin (HE) for general profiling or with Alcian blue at pH 1.0 and eosin counter-staining. For immunohistochemical analysis, antigen retrieval was performed with 0.1% pepsin in 0.02 N—HCl for 10 minutes, and sections were incubated with blocking solution (0.1 M NaPB, 1% BSA and 10% normal goat serum) for 1 hour and then with primary antibodies against phospho-Smad1/5/8 (Cell Signaling Technology™, 9511, 1:100) overnight at 4° C. The antibodies were visualized using rabbit specific HRP/DAB (ABC™) detection kit (Abcam™, ab64261). After detection, sections were counter-stained with 0.5% methyl green.

F. Analysis by μCT

After fixation, samples were subjected to μCT analysis using a CT35 scanner (SCANCO USA™ Inc., Southeastern, PA) at 55 kV and 70 mA for bone volume/tissue volume (BV/TV) analysis. Normalized BV/TV means were calculated by ratios of experimental versus control values.

G. Immunoblotting

ATDC5 cells were grown until approximately 70% confluence in Dulbecco's modified Eagle's medium/Ham's nutrient mixture F-12 containing 5% fetal bovine serum (FBS). After serum deprivation (0.3% FBS) for 16 hours, cultures were treated with rhBMP-2 and/or retinoids for 60 minutes and then lysed in SDS-PAGE sample buffer. Cell lysates were denatured, separated onto 10% SDS-page gels and transferred to PVDF membranes (Millipore™, USA). Membranes were incubated overnight at 4° C. with antibodies against phospho-Smad1/5 (Cell Signaling Technology™, 9516, 1:1000), phospho-Smad1/5/8 (Cell Signaling Technology™, 9511, 1:1000), phospho-Erk1/2 (Cell Signaling Technology™, 4370, 1:500), or phospho-p38 (Cell Signaling Technology™, 4511, 1:500), followed by incubation with horseradish peroxidase (HRP)-conjugated secondary antibody (Cell Signaling Technology™, 7074, 1:2000). HRP activity was detected using a SuperSignal™ West Dura Extended Duration Substrate (Thermo Scientific™, USA). Membranes were re-blotted with antibodies against GAPDH (Santa Cruz Biotechnology™, sc-32233, 1:1000) for loading normalization.

H. Reporter Assays

Primary mouse epiphyseal chondrocytes were isolated from neonatal C57BL/6J mice according to known methods (Yasuhara et al., Lab. Invest. 91(12):1739-1752, 2011) and were plated on 48- or 96-well plates and serum-starved overnight. Cultures were co-transfected with canonical BMP signaling reporter Id1-Luc or retinoic acid response element (RARE)-Luc plasmids and phRG-TK (Promega™) using Lipofectamine LTX™ and Plus™ reagent (Invitrogen™) according to the manufacturer's protocol. Twenty four hours later, cells were treated with rhBMP-2 and/or retinoid and incubated for an additional 24 hours. Cells then were harvested and subjected to dual luciferase assay (Promega™). Firefly luciferase activity was normalized to renilla luciferase activity generated by phRG-TK.

I. Statistical Analysis

All results were examined by one-way factorial ANOVA followed by Dunnett's or Bonferroni's post hoc multiple comparison tests (Prism 5; GraphPad™ Software Inc., La Jolla, CA). p-values less than 0.01 were considered as statistically significant versus control (*p<0.01, as indicated by brackets).

Example 2. Production of RARγ Prodrugs

Scheme 1. Synthesis of Conjugate MM 11253 - Acetaminophen.

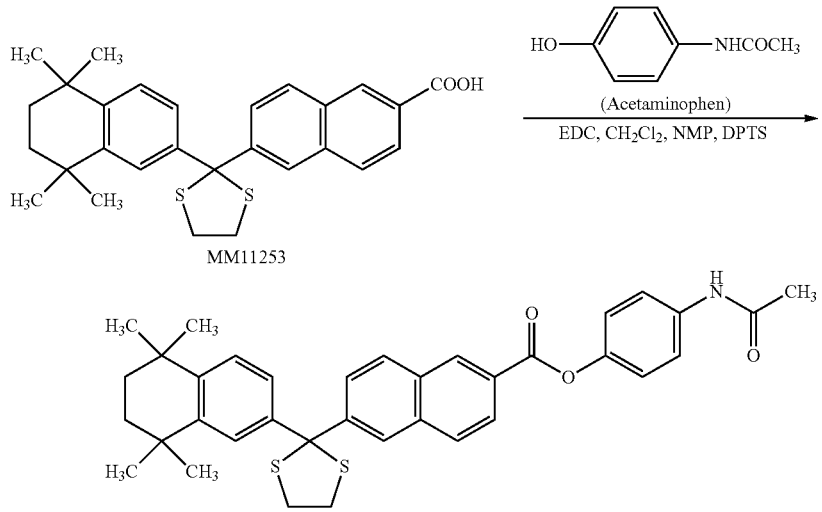

Scheme 2. Coupling of Palovarotene and Acetaminophen.

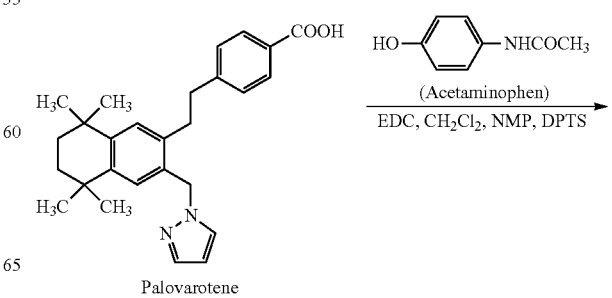

-continued

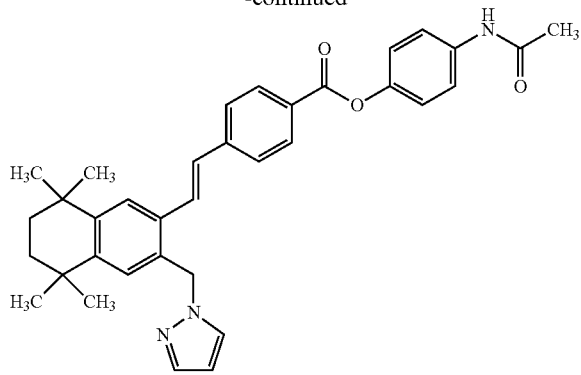

For conjugation of MM 11253 with acetaminophen, the following procedure was used. Under argon atmosphere, MM 11253 (Abcam Biochemicals™, Cambridge, MA, 51 mg, 0.11 mmol), acetaminophen (Alfa Aesar™, 98%, 34 mg, 0.22 mmol) and DPTS catalyst (55 mg, 0.19 mmol) in NMP (1.9 mL) were cooled in an ice-water bath, and EDC (65 mg, 0.34 mmol)) followed by $CH_2Cl_2$ (0.7 mL) were added. The mixture was stirred in the bath for 15 minutes, warmed to room temperature (becoming homogeneous) and further stirred for 22 hours. Aqueous 16% $NaH_2PO_4 \cdot H_2O$ (25 mL, acidified with phosphoric acid to pH 3) was added, the mixture was extracted with ethyl acetate (20 mL), the organic phase was washed with 5M aqueous NaCl (2×50 mL), with water (2×5 mL) and dried. The crude product was purified by flash chromatography (silica-gel, chloroform-acetonitrile, 100:0 to 10:1). Yield of conjugate: 57 mg (89%). $^1$H NMR (400 MHz, $CDCl_3$) and TLC (silica-gel plate, chloroform-acetonitrile, 7:3) confirmed the structure and the purity of compound.

The prodrug conjugate of palovarotene with acetaminophen will be prepared analogously, as shown in Scheme 2. An alternative to acetaminophen prodrugs is to form a phenolic ester prodrug with methyl salicylate.

Figure 2:
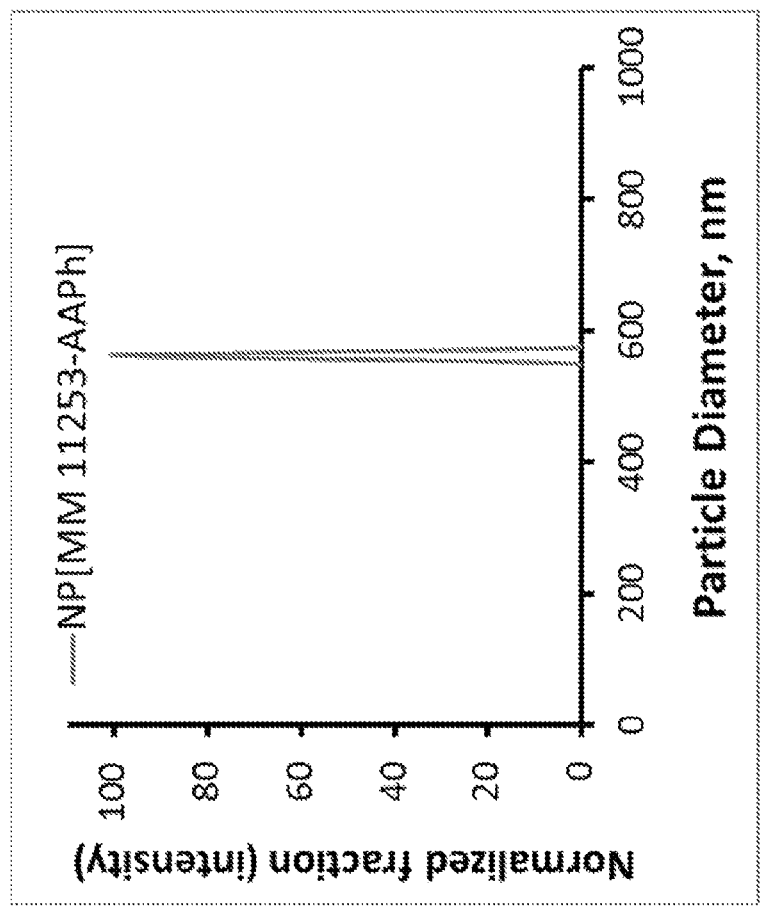
FIG. 2 is a graph showing uniformly sized, drug-loaded nanoparticles.

The MM 11253 prodrug compound exhibited excellent compatibility with PLA-based NP, yielding uniformly sized particles with an average size of 565 nm (polydispersity index<0.1) and the drug loading of 1 mg/ml corresponding to a 67% entrapment yield. See FIG. 2.

Example 3. Expression of RARγ in Long Bone

Figure 3:
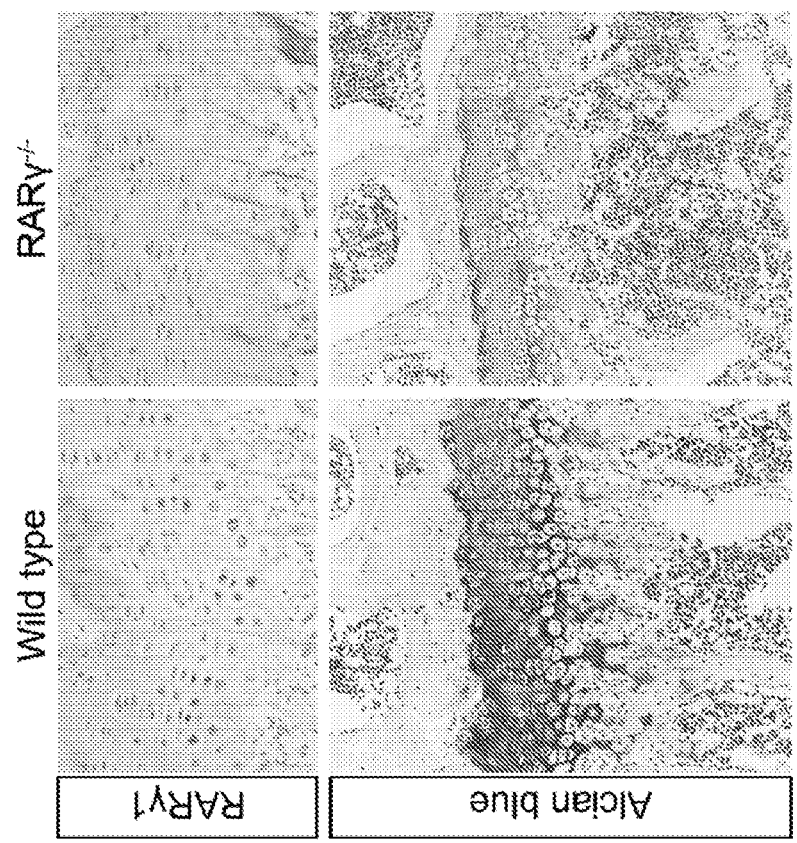
FIG. 3 is a set of longitudinal 6 μm sections of tibias from 5-week-old wild type or RARγ null mice, stained with anti-RARγ antibody or Alcian Blue, showing the presence of RARγ in growth plate.

Using the transgenic mouse mutants for specific retinoic acid receptors (RARα, RARβ and RARγ) and selective RAR agonists and antagonists, it was demonstrated that RARγ is the dominant receptor in GP among three RARs, and chondrocytes are the only cell type that expresses detectable amount of RARγ in long bone. See FIG. 3, which shows a set of longitudinal 6 μm sections of tibias from 5-week-old wild type or RARγ null mice, stained with anti-RARγ antibody. RARγ is shown in growth plate. Selective RARγ agonists also induce expression of numerous matrix metalloproteases and mineralization related genes.

Figure 4C:
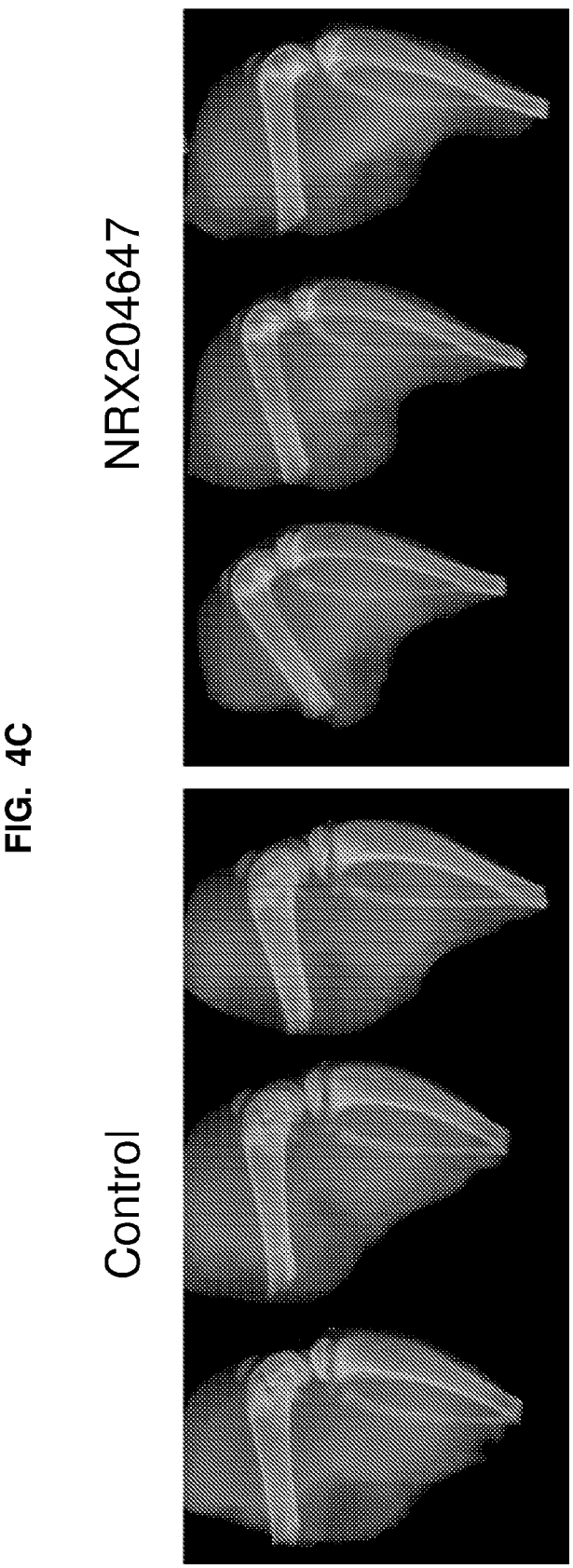
FIG. 4C is a set of X-ray images of the hind limbs of control and NRX-treated mice.

Example 4. Systemic Administration of RARγ Agonist Induces Growth Inhibition and Growth-Plate Closure P11 mice received AM580 (RARα agonist 4 mg/kg), CD2314 (RARβ agonist 4 mg/kg), NRX204647 (RARγ agonist 1.2 mg/kg) or Vehicle (control) on day 12 (Day 1), 14 (Day 3) and 16 (Day 5) by oral gavage. FIG. 4A shows a comparison of body sizes between treated and control mice on day 8. FIG. 4B shows histology sections of tibial growth-plate in control and NRX204647 (agonist)-treated mice at the indicated time points. FIG. 4C shows soft X-ray images of the hind limbs of control and NRX-treated mice from the same experiments. Distal femur and proximal tibial growth-plates were closed in NRX treated group. Systemic administration of RARγ agonists thus facilitated cartilage to bone transition and induced closure of GP in young mice.

Example 5. Inhibition of Injury-Induced Heterotopic Ossification in with Oral Palovarotene AcvrlcR206H/+; R26-rtTA; tetO-cre mice, treated with doxycycline to induce global expression of AcvrlcR206H/+, were subjected to hindlimb muscle injury with cardiotoxin and examined by μCT imaging 14 days after treatment with palovarotene (right) or vehicle (left). Palovarotene was given daily 100 μg/mouse: (20-25 g) (day 1-3) and 15 μg (day 4-14). See FIG. 5, which shows μCT results of untreated (left) and treated (right) mice.

Example 6. Inhibition of RARγ Function Increases the Number of pSmad1/5/8-Positive Cells There are reciprocal antagonistic relationships between the retinoid and BMP signaling pathways in several biological systems. In addition, the suppression of chondrogenesis and heterotopic ossification by RARγ agonists involved inhibition of canonical BMP signaling. Thus, it became important to determine if and how BMP signaling was affected in the various experimental approaches here. Following implantation, mice received vehicle corn oil (Control) or 4 mg/kg CD2665 on day 1 and 3, and ectopic samples were collected on day 5 and subjected to pSmad staining.

Figure 6A:
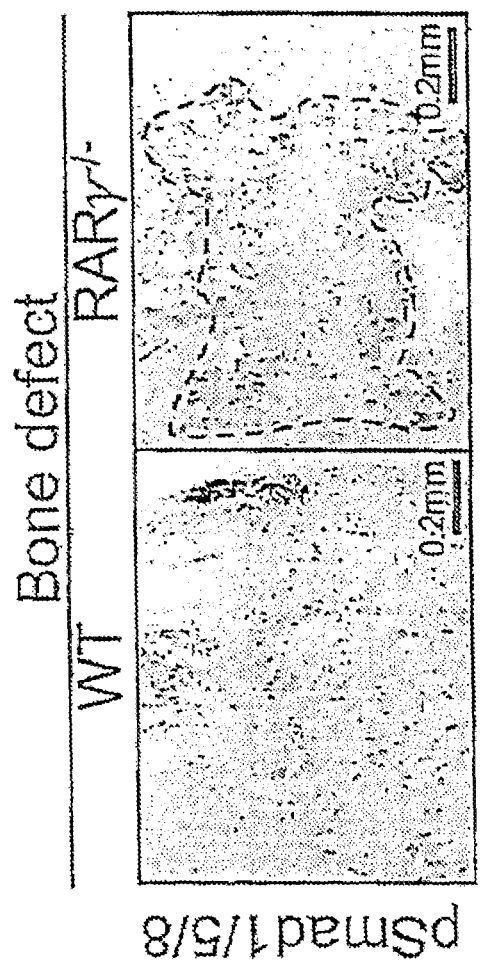
FIG. 6A shows the immunohistochemical detection of pSmad1/5/8-positive cells within bone defects of wild type (WT) and RARγ-null (RARγ$^{-/-}$) tibias 1 week after surgery.
Figure 6B:
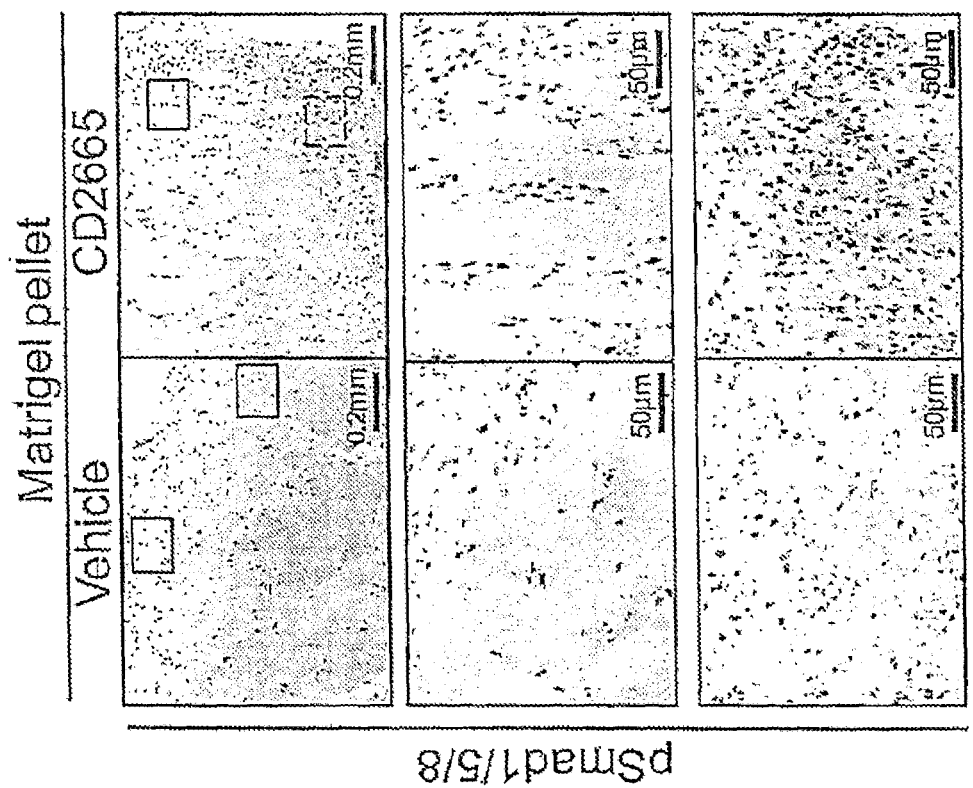
FIG. 6B shows the distribution of pSmad1/5/8-positive cells within ectopic BMP-Matrigel™ masses on day 5 from implantation.
Figure 6C:
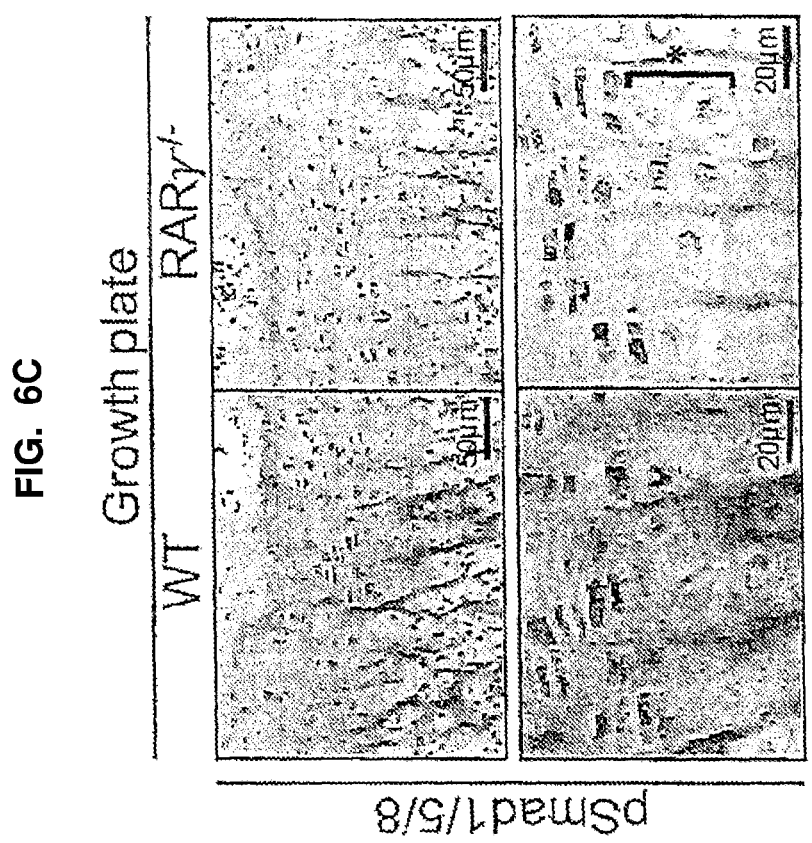
FIG. 6C shows longitudinal sections of growth plate.

First, the distribution of phosphorylated Smad1/5/8-positive cells was determined within regenerating tibial bone defect areas in wild type and RARγ-null mice (FIG. 6A). There were far more numerous and widely distributed pSmad1/5/8-positive cells within the bone repair region in mutant than control mice on day 7 from surgery (FIG. 6A). In an analogous manner, pSmad1/5/8-positive cells were more numerous and obvious in ectopic BMP-Matrigel™ tissue masses from mice treated with RARγ antagonist CD2665 than controls on day 5 after implantation (FIG. 6B). This increase was evident for cells seemingly migrating into the scaffold as well as those surrounding it. Thus, canonical BMP signaling is increased by deficiency of RARγ or by treatment with RARγ antagonists. FIG. 6C shows longitudinal sections of growth plate.

Top panels in FIG. 6 are lower magnified images. Middle and bottom panels are higher magnification of regions indicated by the solid (middle) and dotted (bottom) lines. These results show that inhibition of RARγ function enhances phosphorylation of Smad1/5/8.

Increases and decreases in endochondral bone formation respectively elicited by RARγ antagonists or agonists are accompanied by reciprocal changes in BMP signaling. This is likely to be the key mechanism of RARγ action as BMPs and BMP signaling normally play indispensable roles in endochondral ossification. RARγ modulates cellular function through regulation of target genes (genomic action) as well as via interactions with other signaling pathways (non-genomic action). Here, changes in phosphorylation levels of Smad proteins were observed within 1 hour after RARγ agonist or antagonist treatment in cultured cells. This rapid change indicates that the effects are at least partly mediated by the non-genomic function of RARγ rather than through genomic action that would require changes in gene expression and production of new proteins, both likely requiring more than 1 hour.

Example 7. Expression of RARγ in Growth-Plate Chondrocytes and Cells in BMP-Matrigel™ Masses Five-week-old mouse tibias (WT and RARγ null) were examined by immunohistochemistry for RARγ. Distribution of RARγ in cartilage, as a positive control, and in cells in ectopic BMP-Matrigel™ tissue masses also was examined (see FIG. 7). RARγ is highly expressed in growth plate chondrocytes in wild type mice (FIG. 7A) while not detected in RARγ null mice (FIG. 7B). Expression of RARγ was observed in chondrocytes within the BMP-Matrigel™ tissue masses (FIG. 7E and FIG. 7F).

Example 8. RARγ Antagonists Enhance BMP Signaling in ATDC5 Cells and Primary Chondrocytes RARγ was examined for whether it has cell-autonomous roles on BMP signaling in chondrocytes. Freshly isolated chondrocytes isolated from neonatal mouse cartilaginous long bone epiphyses were treated in culture with increasing concentrations of RARγ antagonists (CD2665 or MM11253) for 24 hours in the absence or presence of 10 ng/mL rhBMP2 and subjected to immunoblot analysis. See FIG. 8A. ATDC5 cells were seeded at a density of $4\times10^4$ cells/16 mm well and maintained in 0.3% FBS DMEM overnight. Cells were then treated with indicated amounts of CD2665 or MM11253 for 1 h in the presence of 10 ng/mL rhBMP-2. Levels of phosphorylated Smad1/5, p38 and Erk1/2 were analyzed by immunoblotting. Membranes were re-blotted with anti-GAPDH antibody for normalization. The pSmad1/5/8 levels were significantly enhanced by RARγ antagonist treatment at each dose tested (FIG. 8A, pSmad1/5).

BMP2 is also known to stimulate the MAPK pathways. Treatment with RARγ antagonists moderately increased the levels of phosphorylation p38, and did not affect Erk1/2 phosphorylation appreciably (FIG. 8A, pp38 and pErk1/2).

Figure 8B:
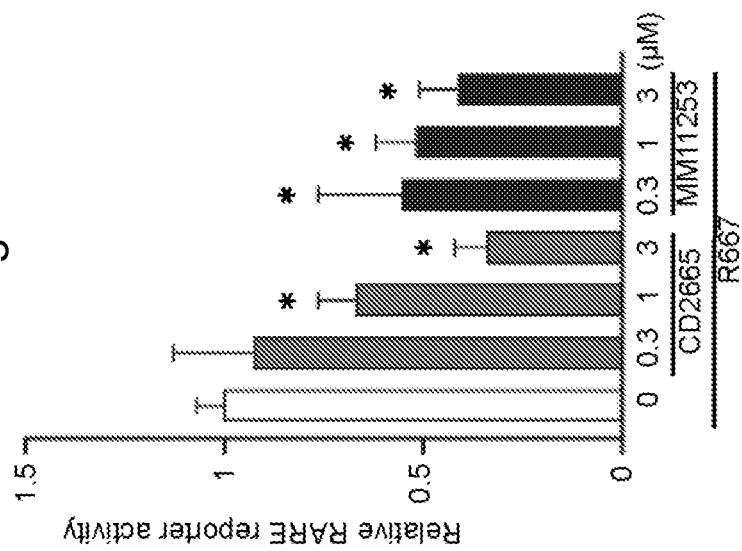
FIG. 8B is a bar graph showing relative Id1 reporter activity.

Enhancement of BMP-Smad signaling by RARγ antagonists was confirmed by Id1-luc reporter assays. Cells were treated with the indicated doses of CD2665 or MM11253 in the absence or presence of 10 ng/mL rhBMP-2. The activity of this reporter was slightly increased by RARγ antagonist treatment in absence of exogenous rhBMP-2 but was significantly enhanced in its presence (FIG. 8B).

Figure 8C:
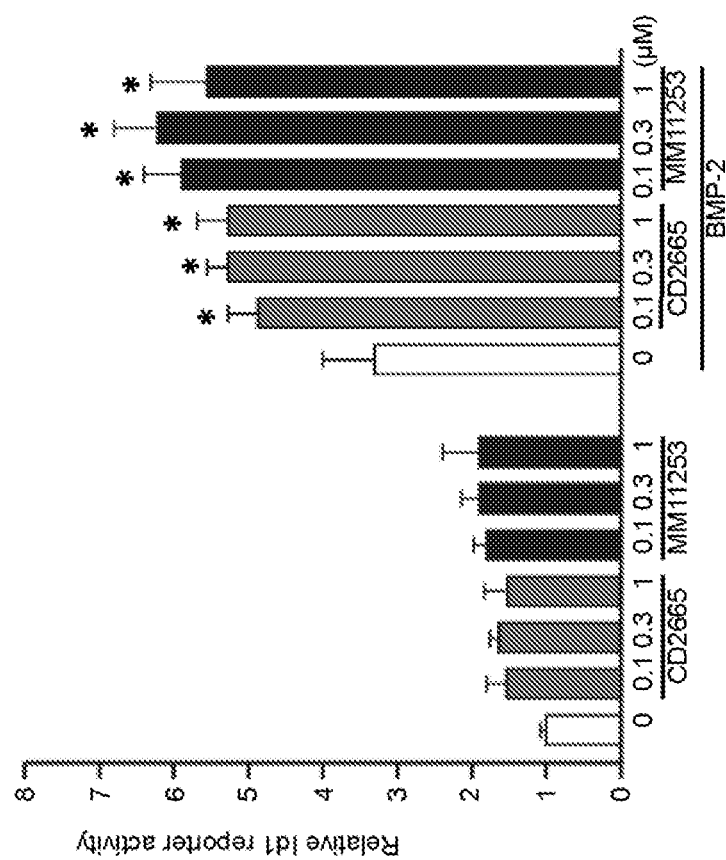
FIG. 8C is a bar graph showing relative RARE reporter activity.

Specificity of responses was confirmed by the fact that the RARγ antagonists inhibited RARE-luc reporter activity (FIG. 8C). Monitoring activity of RARγ antagonists by RARE reporter assay. Cells were treated with indicated doses of CD2665 or MM11253. To detect the effect of RARγ antagonists in retinoid deficient culture condition (0.3% FBS DMEM), 10 nM RA was added to all cultures in experiments reported in FIG. 8A, FIG. 8B and FIG. 8C.

Example 9. Distribution of Locally Injected Fluorescently-Labeled NPs in Musculoskeletal Tissue A nanoparticle drug delivery system was developed that stays locally at the injected site and releases the drug over a prolonged time period. These optimized, biodegradable nanoparticles (NPs) use a poly(D,L-lactide)(PLA) structure. See Alferiev et al., Biomaterials 51:22-29, 2015. The PLA-based NPs, herein called PLA-NPs, are biodegradable and are suitable for entrapping small hydrophobic molecules (therapeutic agents) and their local delivery and sustained release. For information on these particles generally, see Alferiev et al., Biomaterials 51:22-29, 2015; Tengood et al., Proc. Natl. Acad. Sci. USA 111(11):4245-4250, 2014; Baron et al., Anat. Rec. 208(1):137-145, 1984; and Hind and Stinchcombe, Curr. Opin. Invest. Drugs 10(11):1243-1250, 2009.

Figure 9A:
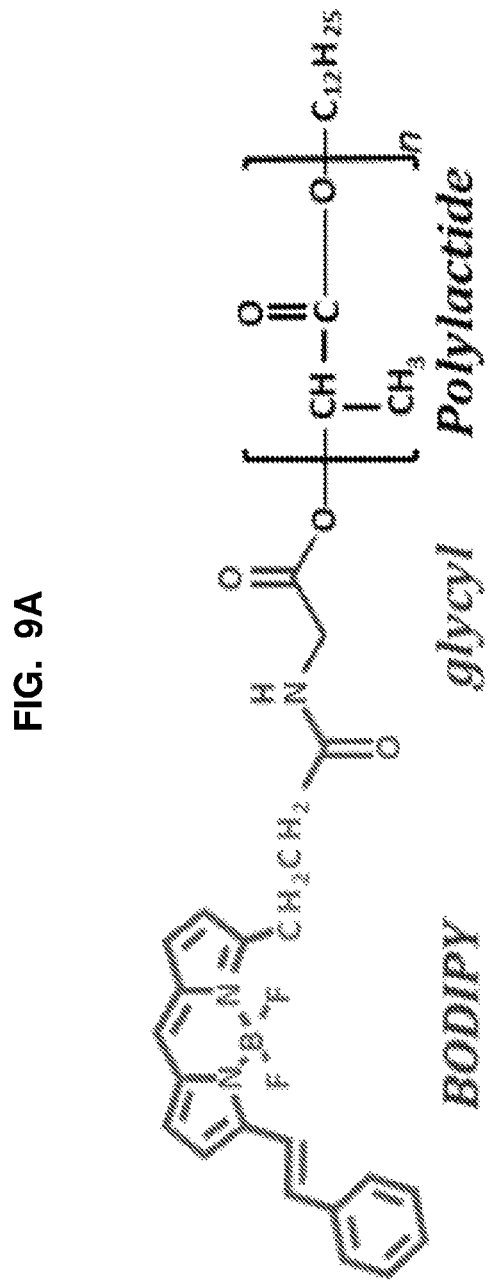
FIG. 9A provides the chemical structure of PLABODIPY (BODIPY-glycyl-polylactide) conjugate.

To examine retention of the NPs in musculoskeletal tissue, stable fluorescently labeled NPs were produced by covalently linking PLA with BODIPY558/568 (see FIG. 9A) and injected inside the tibia (see FIG. 9B and FIG. 9C), into the quadriceps muscle (see FIG. 9D and FIG. 9E), or the vicinity of the growth plate (see FIG. 9F and FIG. 9G) in mice. The result in FIG. 9F and FIG. 9G shows that the NPs are retained for a long time after site-specific injection. The fluorescence was retained at the injected sites for at least one week after injection without obvious signs of inflammation (see FIG. 9), indicating that the PLA-NPs are biocompatible with musculoskeletal tissues and can be used as site-specific drug carriers. Importantly, from a chemical viewpoint, the synthetic RARγ agonists/antagonists are a family of hydrophobic small molecules (350-400 Da) highly compatible with entrapment in NP, which in turn can protect these compounds from inactivation and allow their sustained release spatially restricted to the site of administration. In summary, the results showed that the fluorescently-labeled NPs were retained in both muscle and bone for a prolonged time period after injection to those locations.

Example 10. Comparison of Bioactivity of NRX204647 Solution and NRX204647-Loaded Nanoparticle (NRXNP)

Primary mouse chondrocytes were seeded at high density and maintained for 1 week. RARγ agonists are very potent catabolic agents, while antagonists have the opposite effect. The staining intensity was measured and analyzed by Image J™ to produce a sensitive and quantitative matrix degradation assay. The results can be used to evaluate the effective dose and duration of the test drugs on cartilage growth or degradation in vivo.

To obtain primary chondrocytes for the assay, breeding pairs of mice were maintained to obtain primary chondrocytes from new born pups (P1-5, males and females). In addition, frozen cell stocks of chondrocytes were stored after expansion. To expand the cultures, bFGF was added to the culture medium. Although the primary chondrocytes partially lose their original phenotype after storage, cells still express RARγ predominantly over other RARs and express cartilage matrix genes, and therefore can be used for the reporter assay.

Mature chondrocyte cultures treated with NRX204647 were evaluated for reduction of cartilage-matrix by staining with Alcian Blue. After confirming accumulation of cartilage-matrix (proteoglycan), cells were treated with the indicated dose of NRX204647 solution or NRX-NP suspension that contains comparable amount of NRX204647, as indicated on the left of FIG. 10, for 4 days. The degree of reduction of cartilage matrix was evaluated by Alcian blue staining at pH 1.0. NRX204647 solution (positive control) and NRX-NP treatment decreased Alcian Blue staining similarly in dose dependent manner, indicating this NP formulation fully retained drug activity.

Example 11. Long Term Stability of Bioactivity of NRX204647 in an NP Formulation Primary mouse chondrocytes were isolated and transfected with the RARE-luc reporter gene by reverse transfection according to known methods. Details of the procedure are described in Cong et al., J. Biomater. Sci. Polym. Ed. 26(11):629-643, 2015. The cells were treated with ethanol (EtOH); freshly prepared 10 nM NRX204647 (NRX 10 nM); 100 nM NRX204647 (NRX 100 nM); 100 nM NRX204647 added to culture medium 1 week prior (NRX 100-7D); vehicle only (None); 1 µL unloaded nanoparticles (Blanc NP); 1 µL NRX204647-loaded nanoparticle suspension (0.9 mg NRX204647/ml in 1× solution) diluted 0.01× (NRX-NP 0.01×); 1 µL NRX204647-loaded nanoparticle suspension (0.9 mg NRX204647/ml in 1× solution) diluted 0.1× (NRX-NP 0.01×); 1 µL NRX204647-loaded nanoparticle suspension (0.9 mg NRX204647/ml in 1× solution) diluted 0.01× and added to culture medium 1 week prior (NRX-NP 0.01×-7D); and 1 µL NRX204647-loaded nanoparticle suspension (0.9 mg NRX204647/ml in 1× solution) diluted 0.1× and added to culture medium 1 week prior (NRX-NP 0.01×-7D). NP 0.01×-7D and NP 0.1×-7D are 7-days stored reagents in culture medium that contains the indicated amount of NRX204647-loaded NP suspension. Cells were subjected to the reporter assay 36 hours after the treatment.

Figure 11:
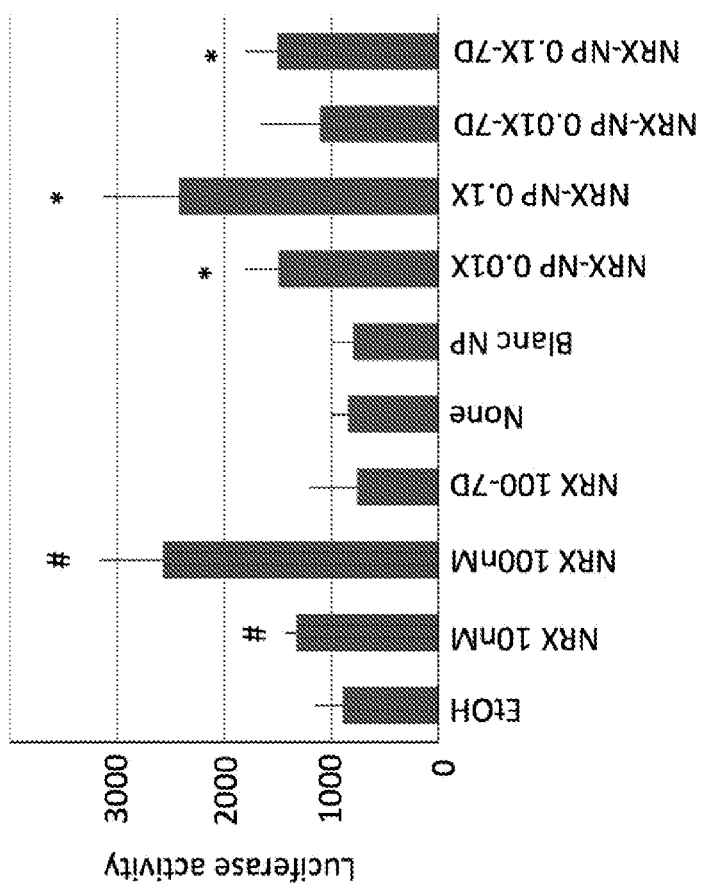
FIG. 11 is a bar graph showing luciferase activity in primary mouse chondrocytes transfected with the RARE-luc reporter gene and treated with the indicated concentrations of NRX204647, an RARγ agonist.

NRX204647 exhibits about 100-fold higher affinity to RARγ compared to other RAR isoforms, and its ED50 is 3-10 ng/mL. Whether its NP formulation preserved biological activity of NRX20467 was tested. Primary mouse chondrocytes were isolated from epiphyseal cartilage in neonatal mice and transfected with the RAR reporter plasmid (RARE-luc) followed by treatment with fresh NRX204647 solution or NRX204647-loaded NPs. Treatment with NRX204647-NPs increased the RARE-luc activity (see FIG. 11; NRX-NP) to a similar degree compared to treatment with NRX204647 solution (see FIG. 11; NRX). When NRX204647 solution or NRX204647-loaded NPs that were suspended in serum free medium and stored for 7 days were tested, NRX solution did not increase the reporter activity (see FIG. 11; NRX-7D), indicating that free compound became inactive in aqueous solution. In contrast, NRX204647-loaded NPs partially retained biological activity (see FIG. 11; NRX-NP-7D), suggesting that the NPs kept releasing the active RARγ agonist into the medium over 7 days.

Example 12. Ectopic Endochondral Ossification in BMP-Matrigel™

Figures 12A, 12B:
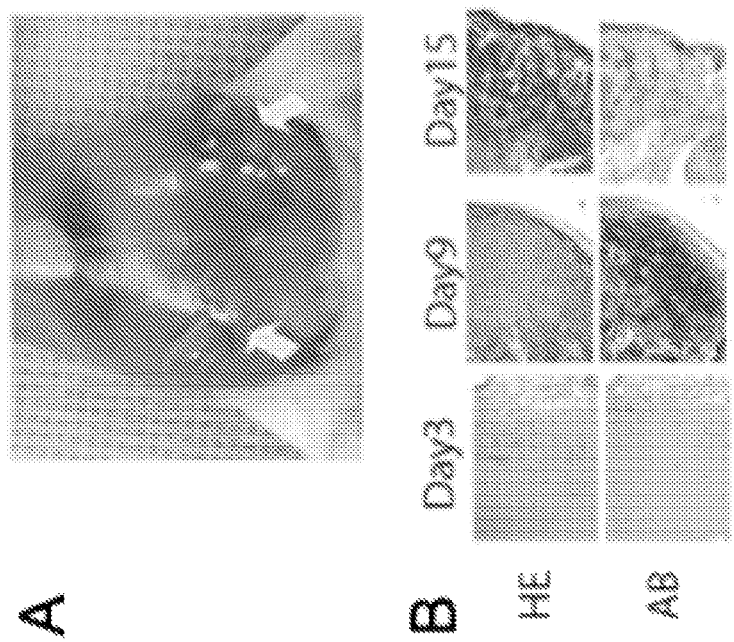
FIG. 12A is a photograph of injected Matrigel™ pellets (arrows) after removal of the skin.
FIG. 12B shows sections of ectopic masses harvested at the indicated time points, stained with HE (top row) or Alcian blue (bottom row).

Recombinant human bone morphogenetic protein-2 (rhBMP-2, 4 µg/ml) was mixed with growth-factor reduced Matrigel, and injected into the subcutaneous abdominal region of 2-month-old CD-1 female mice (see FIG. 12A). FIG. 12B shows histological sections of ectopic tissues 3, 7 and 15 after injection. Host cells invaded into Matrigel™ on Day 3 and organized cartilaginous tissue positive to Alcian blue staining on Day 7. Inductive tissues represented bony structure appeared by Day 15. The time course, histology and the amount of inductive tissue volume were highly reproducible. Preliminary results after a one-time injection of NRX204647-NP containing 3 µg of the active compound inhibited ectopic bone formation to about 30%. This effect approximately corresponds to the effects of systemic administration of the same drug at 30 µg/25 g mouse twice a week in vivo.

Example 13. Selective RARγ Antagonist Enhances Ectopic Bone Formation

To further evaluate the roles of RARγ and the efficacy of RARγ antagonists on bone formation, the effects of three selective RARγ antagonists were compared with the RARγ agonist, NRX204647, using a mouse ectopic bone model. Recombinant human BMP-2 containing Matrigel™ (BMP-Matrigel) was transplanted subcutaneously in the abdomens of CD-1 female mice (ectopic bone formation model). The injected BMP-Matrigel™ mixture rapidly solidified and developed endochondral bone within 10 to 12 days (see FIG. 13B).

Figure 13A:
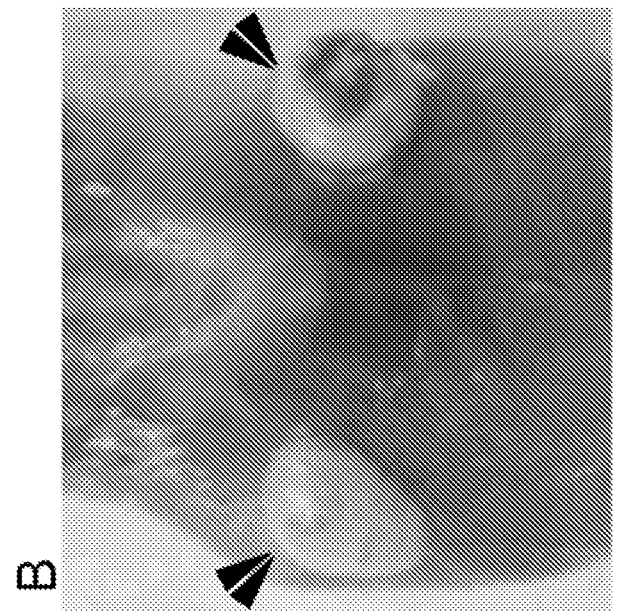
FIG. 13A shows the chemical structures of a synthetic RARγ agonist and synthetic RARγ antagonists.
Figure 13B:
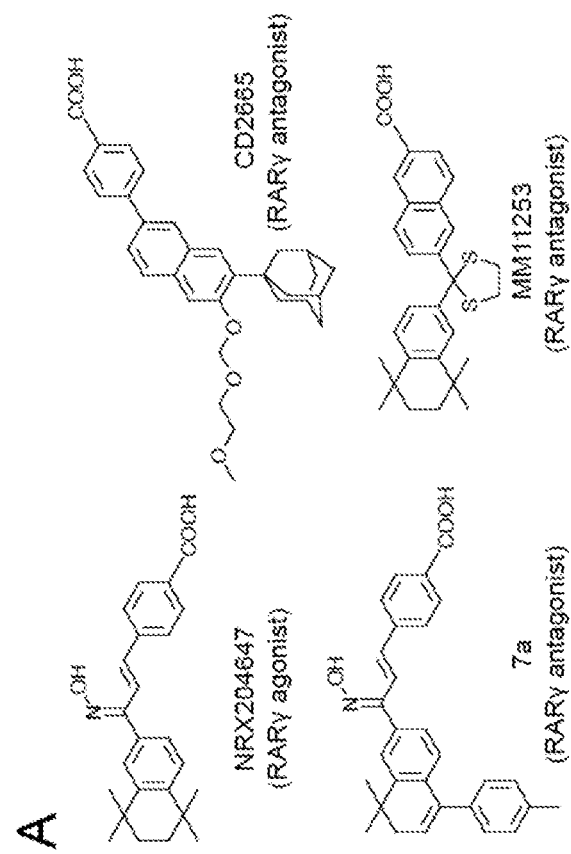
FIG. 13B shows whole mount images of the ectopic BMP-Matrigel™ masses on day 12. The arrowheads point to blood vessels, reflecting ongoing endochondral ossification.

The BMP-Matrigel™ injected mice were randomly subdivided into groups and subjected to oral gavage with vehicle corn oil, RARγ agonist or each of the 3 antagonists on day 3, 5 and 7 (see structures in FIG. 13A). The control mouse with vehicle treatment had inductive masses in the Matrigel™-injected sites (see FIG. 13B). Ectopic tissue masses were collected on day 12 and subjected to X-ray and µCT analyses. Micro-CT images of pellets harvested 12 days after implantation were taken. FIG. 13C. Analysis of µCT images of whole BMP-Matrigel™ pellets showed that these masses were calcified (FIG. 13C, control).

The RARγ agonist NRX204647 strongly inhibited bone formation compared to vehicle-treated mice as determined by µCT analysis (FIG. 13C). In contrast, each of the three RARγ antagonists had significantly increased the amount of detectable bone (FIG. 13C and FIG. 13D). Because the three antagonists are representative of the different backbones characteristic of this drug class (FIG. 13A), the data suggest a stimulatory drug class effect by these retinoids. The number of samples analyzed in this experiment is 8 (NRX204647), 31 (control), 26 (CD2665), 8 (7a) and 6 (MM11253). See FIG. 13C and FIG. 13D. When RARγ agonists were administrated from Day 7 (cartilage forming stage), the degree of inhibition of ectopic bone was lowered, indicating that RARγ agonists primarily inhibit ectopic bone formation by acting on the initial step, induction of ectopic cartilage. In contrast, systemic administration of RARγ antagonists increased the volume of inductive bone (see FIG. 13C and FIG. 13D).

To verify specificity of this drug action, similar ectopic bone formation experiments were carried out with RARγ-null mice treated with vehicle or one of the antagonists (CD2665) (FIG. 13E). No significant differences in bone formation in vehicle-versus drug-treated mice was observed, indicating that the drug action was isotype-specific and that antagonizing RARγ function is indeed required to increase ectopic bone formation (FIG. 13E; the y-axis indicates relative amount of bone compared to the control; N=8).

Figure 14A:
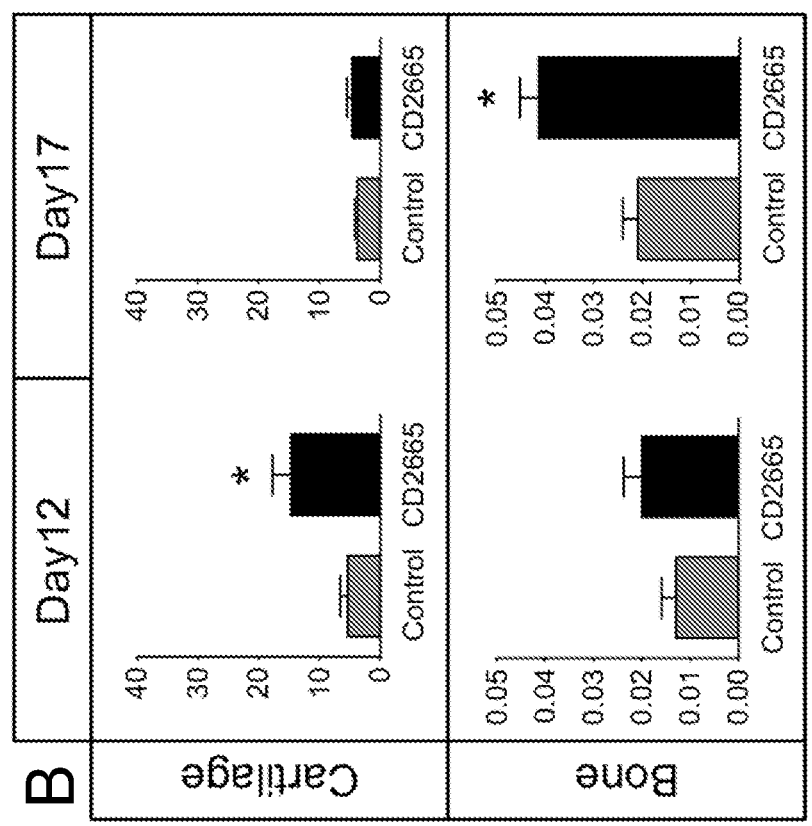
FIG. 14A and FIG. 14B are histograms showing results of systemic administration of RARγ antagonist on cartilage and bone formation in BMP2-Matrigel™ pellets as indicated.

Example 14. Stage Dependent Effects of RARγ Antagonist on Cartilage and Bone Formation in BMP2-Matrigel™ Pellets Mice with Matrigel™ Pellets as described above were administered vehicle or 4 mg/kg CD2665 on day 3, 5 and 7 after BMP2-Matrigel™ transplantation by gavage, and then analyzed on Day 7 or Day 12. FIG. 14A. Separately, a second group of mice were administered vehicle or 4 mg/kg CD2665 on day 7, 9 and 11 after BMP2-Matrigel transplantation and analyzed either on day 12 or 17. Pellets were collected at the indicated time, fixed and subjected to μCT analysis (bottom row). Pellets were then sectioned and stained with Alcian blue for quantitation of cartilage (top row).

Figure 14B:
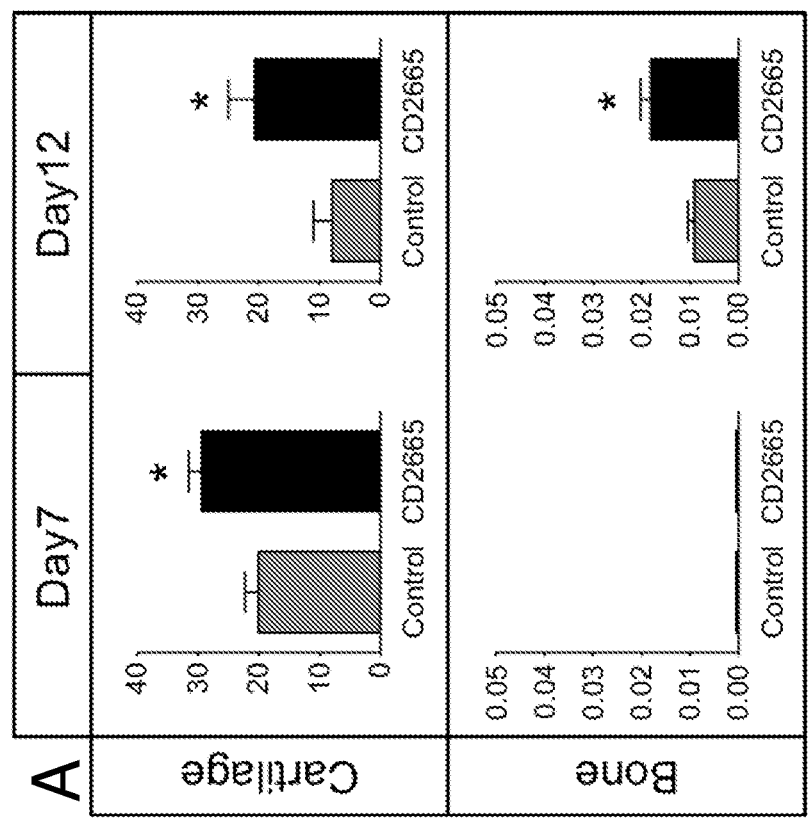

The results of the histomorphometric analysis revealed that RARγ antagonists stimulated both cartilage formation and bone formation when they were administered at the early phase (initiation of chondrogenesis) (FIG. 14A) and the mid phase (cartilage growth) (FIG. 14B). These results indicate that RARγ agonists and antagonists can be used for pharmacological control of endochondral ossification.

Example 15. Action of RAR Antagonists on Phases of Endochondrial Bone Formation To clarify the mode of action of RARγ antagonists on successive phases of the endochondral bone formation process, closer histological and histomorphometric analyses was carried out on ectopic tissue samples collected at different time points from control and RARγ antagonist-treated mice. By day 3 in control mice, the BMP-Matrigel™ scaffold already contained an appreciable number of invading host cells that likely included skeletal progenitors and inflammatory cells. By day 6, a significant amount of Alcian blue-positive cartilage was seen that had increased significantly by day 9 and was being replaced by bone and marrow over time and almost completely by day 20.

Figure 15A:
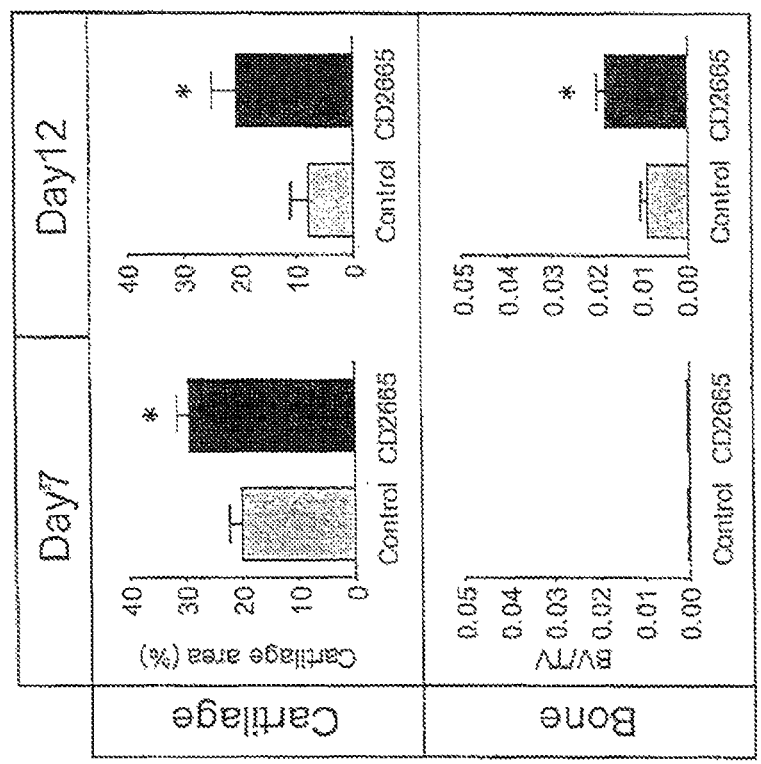
FIG. 15A and FIG. 15B are bar graphs showing quantitation of cartilage and bone in ectopic masses from control and RARγ antagonist-treated mice at the indicated times.

Samples were first subjected to μCT analysis and were then sectioned and stained with Alcian blue for quantification of cartilage. For each group, 3 sections each (1 mm interval of 4 independent samples) were analyzed. Histomorphometric analyzes of ectopic tissue masses from companion mice treated with RARγ antagonist CD2665 as above showed that they contained a significantly higher amount of cartilage than controls on day 7 (FIG. 15A; cartilage; Day 7). While the overall area of cartilage had decreased by day 12, it was still more abundant in treated than control samples (FIG. 15A). Analysis by μCT showed that the mineralized tissue volume was about 2-fold larger in RARγ antagonist-treated than control samples on day 12 (FIG. 15A). These findings indicated that the RARγ antagonists stimulated cartilage formation, representing the early phase of endochondral formation which results in increased bone formation at later stages. For the experiments shown in FIG. 15A, mice were administered vehicle or 4 mg/kg of CD2665 by gavage on day 3, 5 and 7 from BMP-Matrigel™ implantation and samples were collected on day 7 or 12.

Figure 15B:
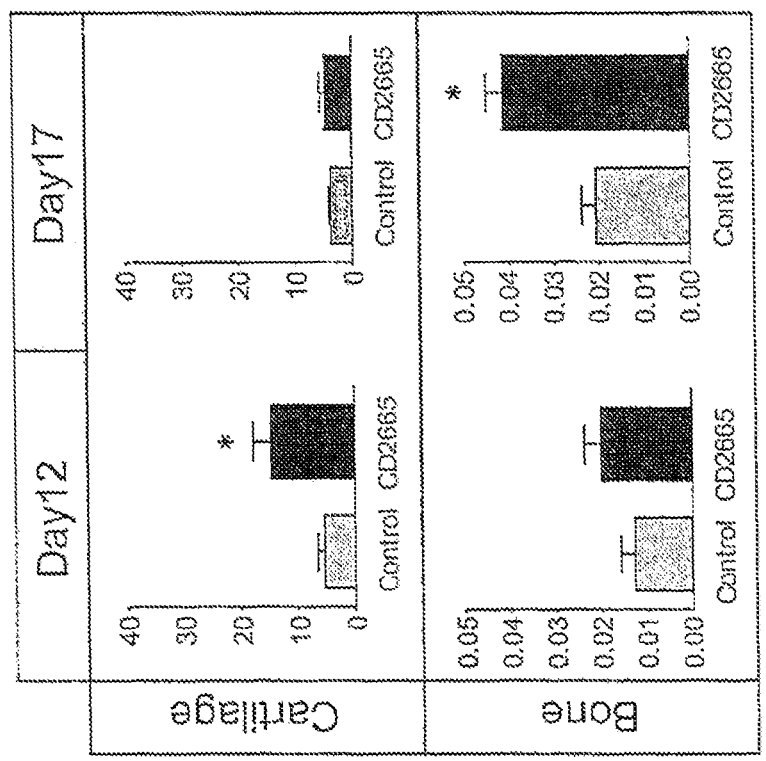

To examine these later stages more closely, mice implanted with BMP-Matrigel™ were treated with a RARγ antagonist on day 7, 9 and 11, and the ectopic tissue masses were analyzed on day 12 or 17 (FIG. 15B). On day 12, more cartilaginous tissue was observed in RARγ antagonist-treated than control samples (FIG. 15B). The amount of mineralized tissue appeared to be increased as well, but the difference was not significant over control values. By day 17, the cartilaginous tissue area was reduced in both groups, but RARγ-antagonist treated samples displayed a significantly larger volume of bone than controls (FIG. 15B). The findings reaffirm that RARγ antagonists enhance cartilage formation during the middle stages of endochondral ossification and eventually lead to increases in bone formation. For experiments in FIG. 15B, mice were administered vehicle or 4 mg/kg CD2665 by gavage on day 7, 9 and 11 from implantation and analyzed on day 12 or 17.

Example 16. Healing of Surgical Tibial Bone Defect is More Rapid in RARγ-Null than Wild-Type Mice Stimulation of RARγ function by selective retinoid agonists had inhibited endochondral bone formation at ectopic sites in HO models, suggesting that RARγ normally serves as a negative regulator of endochondral ossification under similar circumstances. To test this possibility, whether RARγ deficiency would affect and actually stimulate endochondral bone repair was examined. A 1 mm round-shaped hole was created in cortical bone in the upper third region of the tibia (see FIG. 16A) in adult wild-type and RARγ-null (KO) mice and the repair process monitored over time. In control mice at day 7 after surgery, the bone defect was filled with fibrous tissues containing a small amount of cartilaginous nodules that were positive for Alcian blue staining (see FIG. 16D). In contrast, abundant cartilage tissue was found around the perimeter of the defect in companion RARγ-null mice (FIG. 16G). Analyses by μCT and calcein labeling at 2 weeks after surgery revealed that the RARγ-null mice exhibited faster bone healing and higher bone forming activity compared to wild type mice (compare FIG. 16B FIG. 16C and FIG. 16D to FIG. 16E, FIG. 16F and FIG. 16G).

To assess more closely the degree of cartilage formation, serial sagittal sections through the tibias were prepared, stained with Alcian blue and eosin and the cartilaginous regions that had developed within and around the defect were analyzed. The overall areas of cartilaginous tissue were significantly larger in RARγ-null mice than control mice at 1 week from surgery, but dwindled over time as endochondral ossification progressed and cartilage was replaced by bone. We did not quantify bone itself because it was difficult to distinguish repair from endogenous bone in tissue sections. The above data indicate that absence of RARγ leads to a more exuberant cartilage formation and a more rapid bone repair process.

Example 17. Evaluation of Bone Growth by Fluorochrome Labeling

Given that bioactivity of NRX204647-loaded NPs was retained for at least 1 week, whether local administration of NRX204647-loaded NPs affected bone growth at a specifically targeted site was tested. The primary spongiosa, the border of growth plate and bone, is the place where cartilage is replaced with bone. To monitor bone growth, we labeled newly-synthesizing bone with fluorochromes. First, xylenol orange (XO) was injected intraperitoneally into 10-day-old mice followed by an injection of calcein 6 days after the XO injection. On the next day after the calcein injection, the tibia was harvested to examine the bone labeling. The proximal epiphysis (right side of the bone) was dominantly labeled with calcein (green) but not with XO (red), clearly showing the markedly higher activity of new bone formation and remodeling at the proximal site of the tibia. FIG. 17A shows results from a test where mice received xylenol orange 90 mg/kg on day 17 and calcein 30 mg/kg on day 25 by IP injection. The tibia was collected on day 27.

FIG. 17B, FIG. 17C and FIG. 17D show the results of bone labeling with XO (red) for 3 days. P10 mice received xylenol orange 90 mg/kg by IP injection. Tibias were collected on day 12. The magnified images reveal active longitudinal extension of newly formed bone at the proximal tibia. FIG. 17B: fluorescent image; FIG. 17C: superimposed image of fluorescent and bright filed image; FIG. 17D: higher magnification of the indicated area in FIG. 17C.

Example 18. Growth Restriction of Targeted Bone by Local Administration of Retinoid-Loaded Nanoparticles RARγ is highly expressed in GP (FIG. 3) and responsible for the growth arrest in response to excess RA (FIG. 4). Following oral administration of agonists for RAR isoforms or vehicle in P11 mice, the RARγ agonist, NRX204647, inhibited bone growth, resulting in a 15% shorter body length at P18. The bony elements are proportionally shorter in the RARγ-treated group (FIG. 4). Histological examination revealed that the proximal tibial GP of RARγ-treated mice was transiently enlarged with an increase in the width of the hypertrophic zone which closed in 8 days, whereas the samples treated with agonists for other RAR isoforms did not show such changes. Furthermore, NRX204647 treatment down-regulated gene expression of sox families and cartilage matrices and up-regulated MMPs and Rank1, suggesting that the treatment facilitated transition of cartilage to bone by decreasing cartilage matrix production and increasing matrix degradation.

Local delivery of NRX204647 was tested to see if it restricted growth of the targeted bone. To ensure local and sustained delivery of the active drug, NRX204647 was entrapped in PLA-based nanoparticles (NRX-Nano) and injected into the vicinity of the proximal GP of left tibias of 3-week-old mice. The mice were administered NRX204647-loaded NP containing about 4.5 μg NRX204647, injected adjacent to the proximal GP of the left tibia. Right tibias received empty particles. After 2 weeks there was no obvious difference in gross appearance between the treated (left) and non-treated (right) mice (FIG. 18A). X-ray image analysis, however, detected GP closure of the left tibia (arrow, FIG. 18B) and the isolated bones showed an apparent difference in the length between NRX- and PBS-treated bones (FIG. 18C). Side-by-side comparison of control (right side) and NRX-NP treated (left side) bones showed apparent restriction of bone growth by the NRX-NP treatment (FIG. 18D). Histological analysis revealed the height of growth-plate of NRX-NP treated group was remarkably reduced. There was no remnant of cartilage matrix along primary trabecular bones. These findings indicate that the growth-plate in NRX-NP group is essentially arrested (closed) and does not contribute bone growth. In contrast, there was no noticeable change in articular cartilage of NRXNP group (FIG. 18E). The results demonstrated that NRX204647-loaded NPs specifically inhibits bone growth at the targeted bone without affecting growth of other bones.

This is in sharp contrast with mice given NRX204647 by oral gavage that became proportionally smaller than control mice (FIG. 4A). The findings clearly indicate that NPs-based drug delivery is effective at controlling bone growth at a desired site. X-ray analysis detected narrowing of the GP in the NRX-Nano-treated group, and the length of the tibia became shorter in the treated group compared to the control. The results indicate that RARγ agonist-based pharmacological manipulation of the growth of a targeted bone is feasible and can replace growth-restriction surgery for growth imbalance or HO. See FIG. 18.

Example 19. RARγ Agonist Treatment Inhibited Growth of Osteochondromas

Oral administration of RARγ agonist inhibits osteochondroma formation in the HME model mouse. HME mice harbor floxed EXT1 and CreER under the control of the promoter of Col2a1. Local injection of RARγ-NP, therefore can be used for this purpose as well to inhibit/reduce cartilagenous tumors. See FIG. 19, which shows osteochondromas forming in the ulna and radius in the HME mice. Cre activity was induced by injection of tamoxifen at P5-P7. FIG. 19A, FIG. 19B, and FIG. 19C: vehicle control; FIG. 19D, FIG. 19E, and FIG. 19F: RARγ agonists-treated group. Yellow boxes in FIG. 19A, FIG. 19B, FIG. 19D and FIG. 19E represent the areas magnified in FIG. 19B, FIG. 19C, FIG. 19E and FIG. 19F, respectively. RARγ agonist treatment inhibited growth of osteochondromas. Yellow boxes in FIG. 19A, FIG. 19B, FIG. 19D and FIG. 19E represent the area magnified in FIG. 19B, FIG. 19C, FIG. 19E and FIG. 19F, respectively.

Figure 21B:
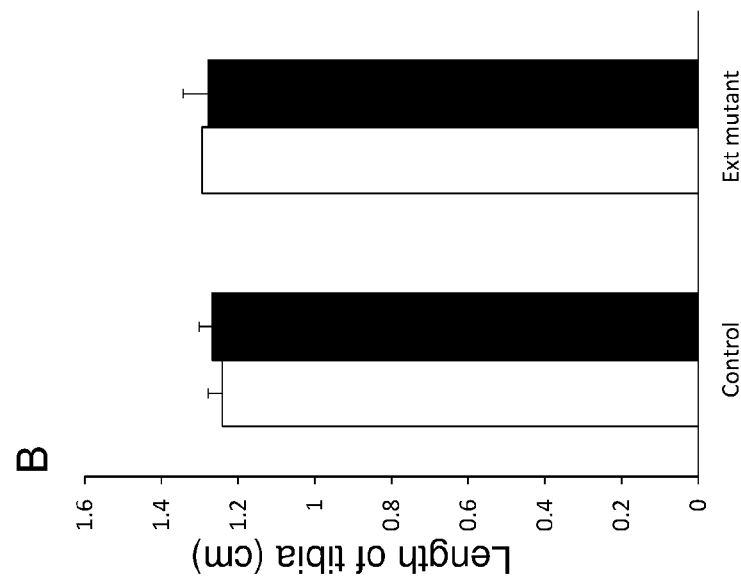
FIGS. 21A-21B are a set of bar graphs showing exostosis area/section (FIG. 21A) and tibia length (FIG. 20-21B) as indicated.
Figure 21A:
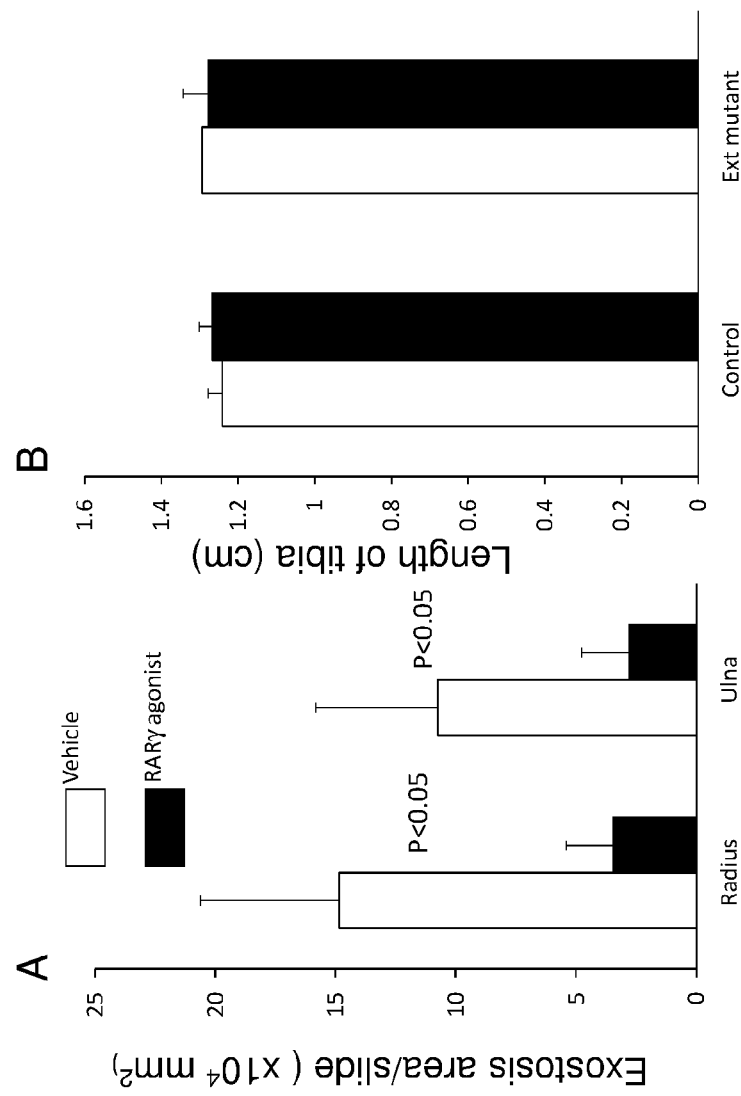

See also FIG. 20 and FIG. 21. FIG. 20 is a set of photographs showing the defined regions of osteochondromas for the quantitative analysis. FIG. 21 is a set of bar graphs showing exostosis area/section (FIG. 21A) and tibia length (FIG. 20-21B). Quantitative analysis of osteochondroma formation revealed that RARγ agonists reduced the size of cartilage tumors. Local injection of RARγ-NP, therefore can be used for this purpose as well to inhibit/reduce cartilagenous tumors. Local injection of RARγ-NP to the vicinity of sporadic or multiple osteochondromas therefore is a treatment that can reduce growth of this tumor by inhibition of further ectopic cartilage formation. This method also can induce replacement of cartilage to bone by acceleration of the hypertrophic phenotype of cartilage tumor cells. Local administration has the advantage to minimize adverse effects of RARg agonists compared to systemic administration.

Example 20. RARγ Antagonist and Agonist Effects on Matrix Production

Cartilage matrix production is enhanced by the pan-retinoid antagonist, AGN194310. See FIG. 22. The limb bud cells were inoculated at a high density and treated with retinoids. Cartilage matrix accumulation was visualized by Alcian blue staining. RA restricts the cartilage forming region, indicating that in the absence of RA or in the presence of an RA antagonist, RAR enhances chondrogenesis and cartilage-matrix production. Similar testing was described in Hoffman et al., J. Cell. Biol. 174:101-113, 2006. Chick limb bud cells were isolated from day 12 embryos, seeded at the density of $4 \times 10^5$ cells in 10 μL and maintained in 1% FBS containing high glucose DMEM for 3 days. Cultures then were treated with 0.1% EtOH (vehicle), retinoic acid (RA) 1 μM or AGN194310 100 nM for 6 days, fixed, and stained with Alcian Blue, pH 1.0.

Figure 23:
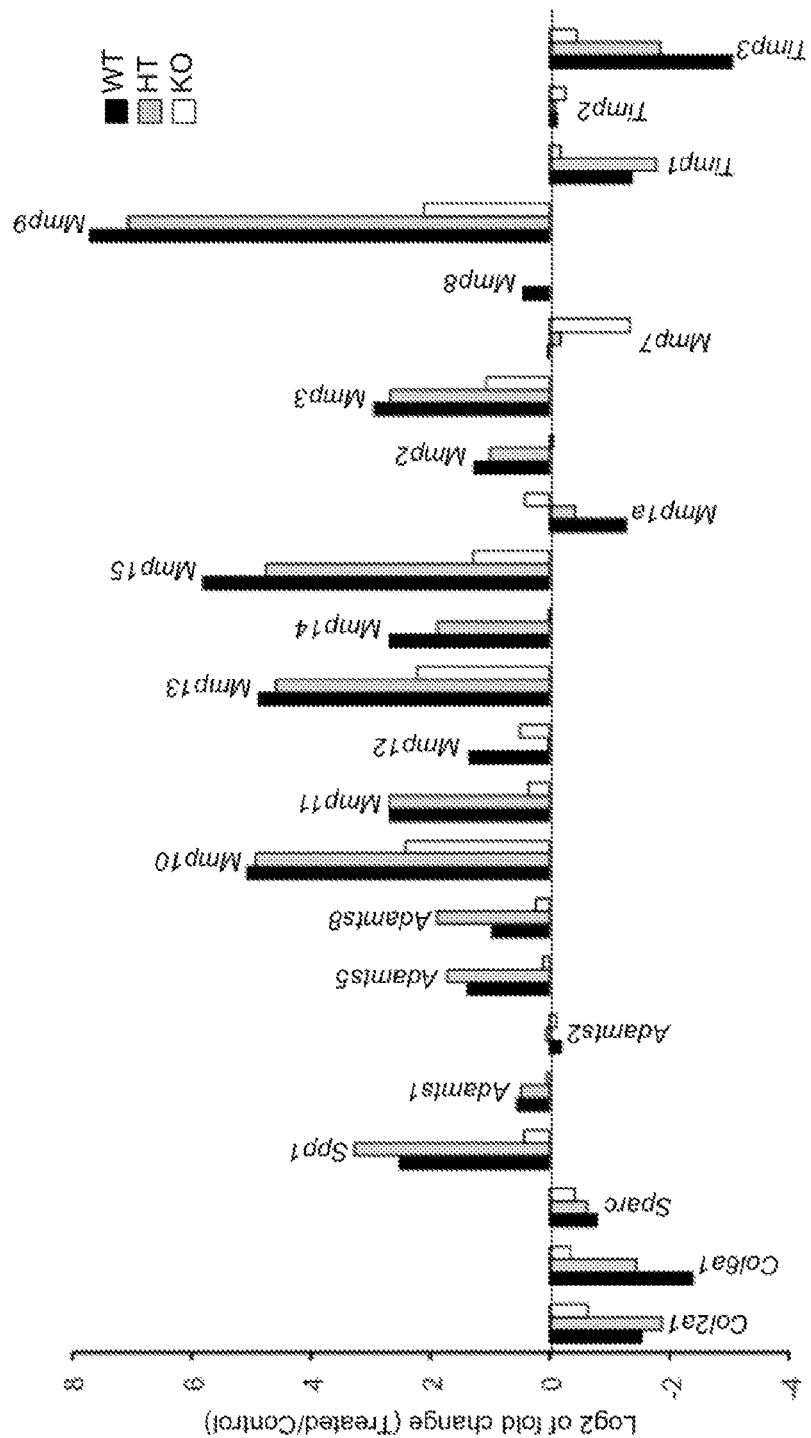
FIG. 23 is a bar graph showing changes in the expression of cartilage matrix molecules and matrix proteases.

RARγ agonist reduces matrix production and promotes cartilage-matrix breakdown. See FIG. 23. Epihyseal chondrocyte cultures prepared from postnatal mice were treated with RARγ agonists and subjected to gene expression analysis by RNAseq™. Primary mouse epiphyseal chondrocytes were isolated from postnatal day 3 wildtype, RARγ hetero (HT, RARγ+/−) and RARγ null (KO, RARγ−/−) mice, seeded onto a 12-well plate ($5 \times 10^5$ cells/well), and maintained with 10% FBS DMEM until confluent. Cells then were treated with 0.1% EtOH (control) or 100 nM RARγ agonist NRX204647 for 48 hours. Total RNA was purified at the end of culture and subjected to Qiagen™ PCR array to analyze the expression profile of cartilage matrix and protease genes. The graph shows relative gene expression levels of indicated genes compared to those in control. Values are averages of 4 samples. NRX204647 treatment markedly decreased cartilage-matrix synthesis while increased variety of matrix degradation enzymes. Such changes were minimum in RARγ null mice.

Example 21. Manipulation of Bone Alignment by Retinoid-Loaded NP

Figure 24C:
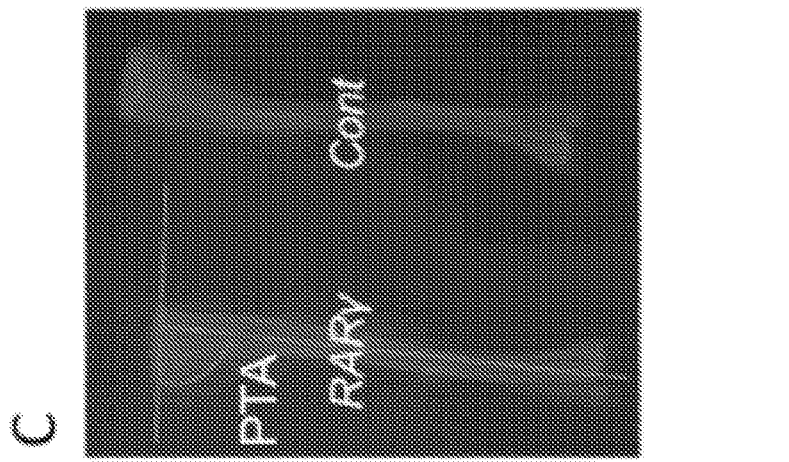
FIG. 24C shows X-ray-based measurements of the angulation of bone (PTA).
Figure 24B:
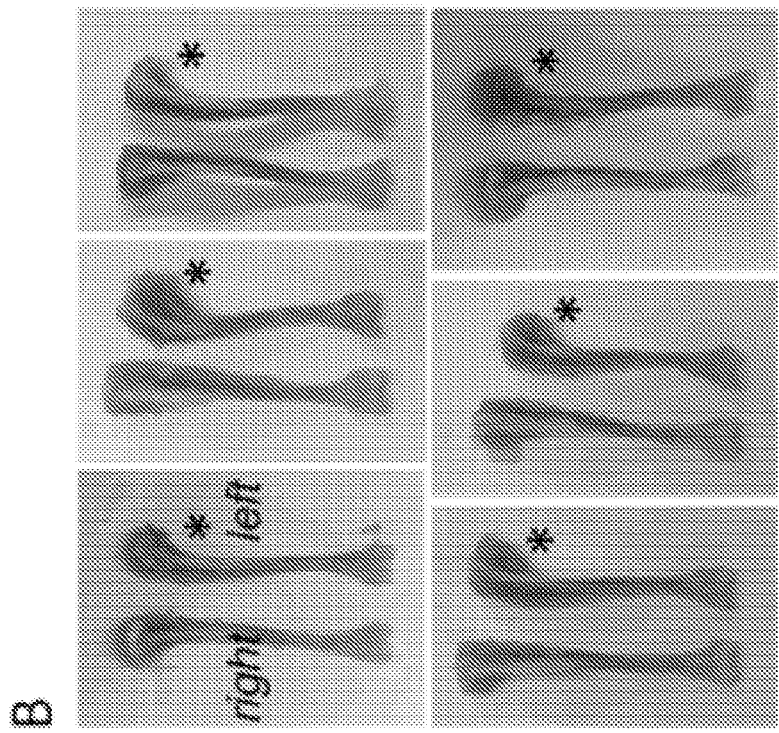
FIG. 24B shows a side-by-side comparison of tibias of control and drug-treated sides from 6 mice.
Figure 24A:
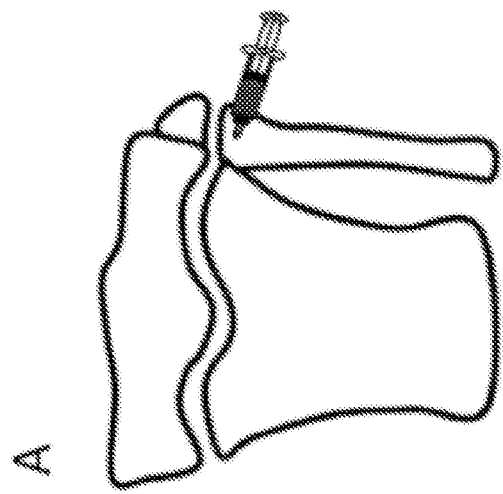
FIG. 24A is a schematic drawing that illustrates the drug injection site.

Mal-alignment of bones and/or joints accounts for a substantial portion of skeletal imbalance. The feasibility of retinoid-loaded NP based correction of bone alignment was examined About 3 μg of NRXNP was injected into the lateral side only of proximal tibial growth-plate in 3-week-old mice. The right tibia was used as a control. Tibias were isolated at 8 weeks and subjected to visual comparison and measurement of angulation. At 8 weeks, the joint surface of the drug treated tibia was tilted toward the lateral side. The proximal tibial angle (PTA, defined as the angle between the mechanical axis and proximal articular surface) was evaluated radiographically. The PTA of treated tibia was 6.8° less than those of control tibia ($p<0.05$; n=6). See FIG. 24.

Figure 25:
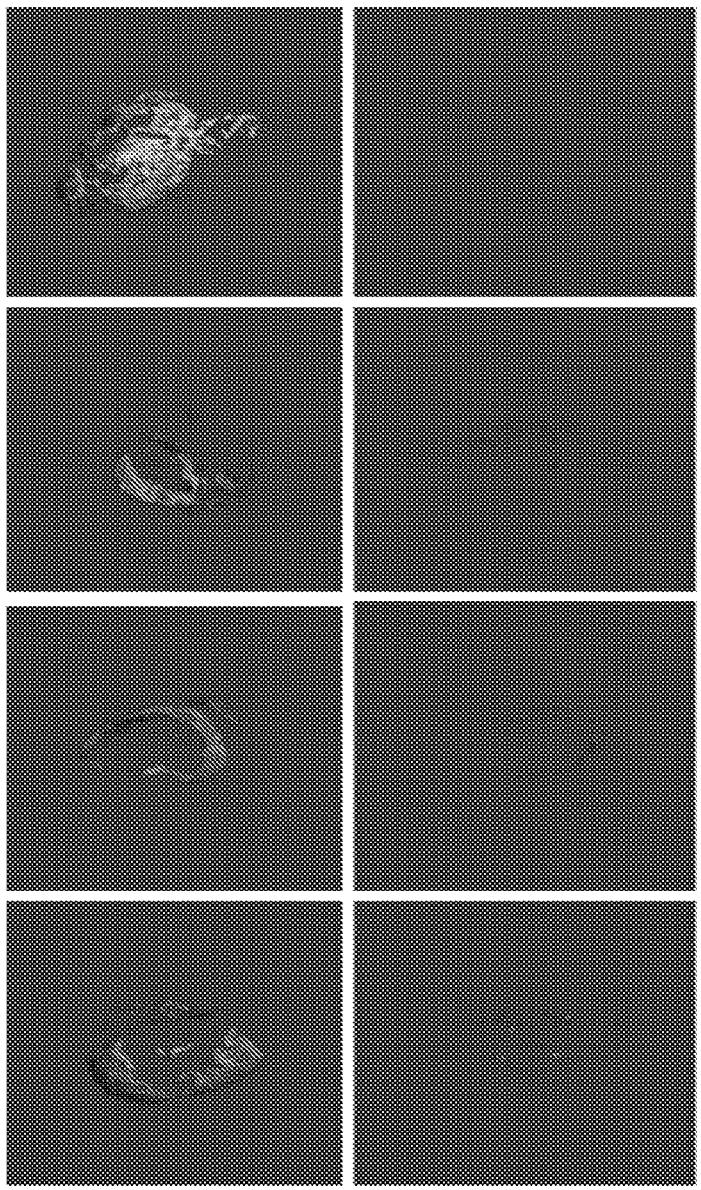
FIG. 25 is a set of μCT images of ectopic bones induced in BMP-Matrigel™ isolated from control or NRX-NP injected mice.

Example 22. Potent and Prolonged Inhibition of Heterotopic Ossification by Locally Injected RARγ Agonist-Loaded NP Subcutaneous transplantation of 1.0 μg rhBMP-2 containing Matrigel™ (0.2 mL) in the abdomens of 2-month-old CD-1 female mice was performed. On day 3, 5 μL of empty NP or NRX204647-loaded NP (NRX-NP; containing 4 μg NRX204647) were injected around the pellets. On day 12, pellets were subjected to μCT analysis. The average amount of ectopic bone (BV/TV)+/−SD in the control was 0.03725+/−0.01379. The average amount of ectopic bone (BV/TV)+/−SD in NRX204647-NP was 0.00055+/−0.000342. Note that a one-time injection of NRX-NP reduced BMP-induced ectopic bone formation (*$p<0.01$; n=4). See FIG. 25. Thus, locally injected RARγ agonist loaded NP showed potent and prolonged inhibition of heterotropic ossification.

Example 23. Enhancing Endochondral Ossification by RARγ Antagonist-NP

Figure 26A:
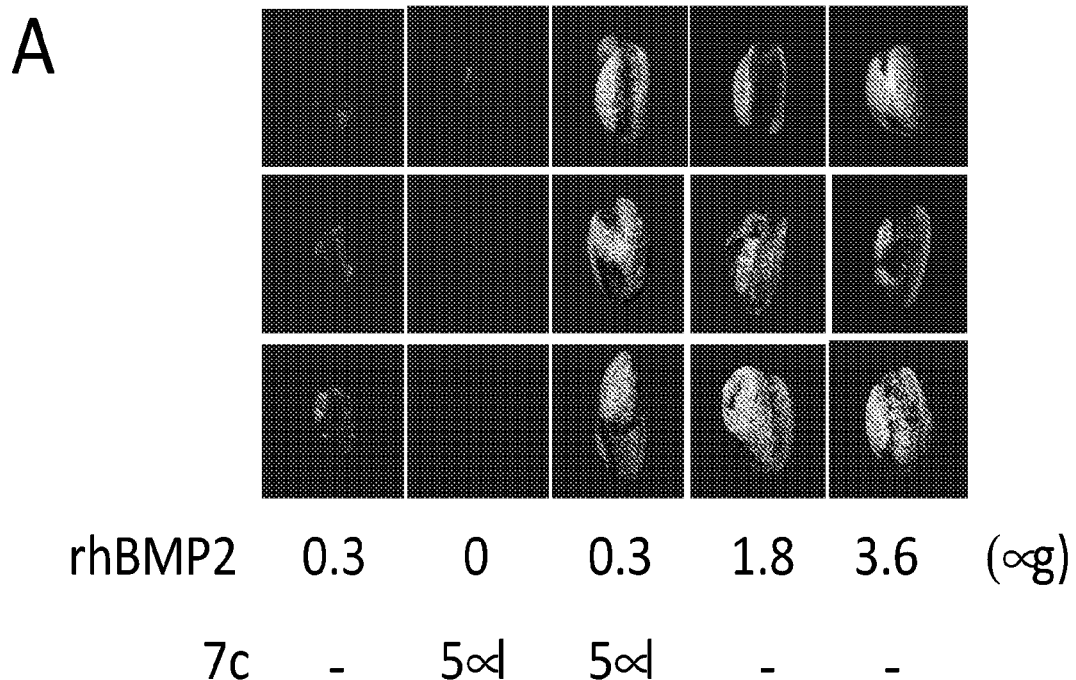
FIG. 26A shows μCT images of corrected ectopic bones after RARγ agonist treatment.
Figure 26B:
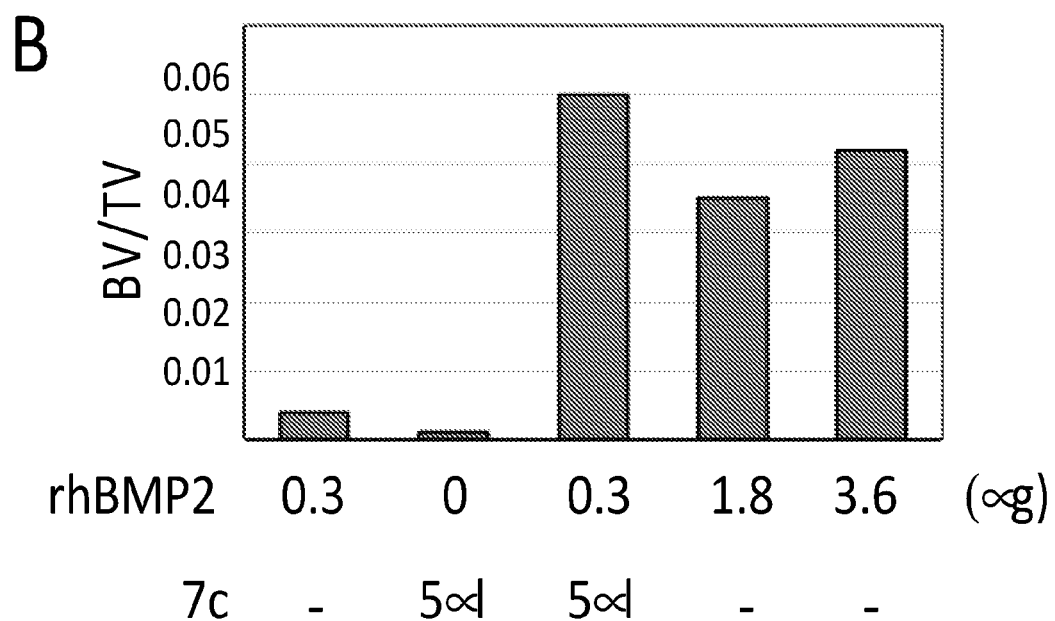
FIG. 26B shows the results of quantitation of ectopic bone expressed in terms of BV/TV.

Subcutaneous transplantation of rhBMP-2 containing Matrigel™ (BMP-Matrigel™) pellets in the abdomens of 2-month-old CD-1 female mice was performed. On day 3 and 10, 5 μl of empty NP or 7c-loaded NP (7c-NP: 3.5 μg in 5 μl) were injected around the Matrigel™ pellets. Ectopic bone tissue was corrected on day 15 and subjected to μCT analysis. FIG. 26A shows μCT images of pellets harvested 15 days after transplant indicating the effect of RARγ agonist on ectopic bone formation in Matrigel™ (the Matrigel™ pellets were mixed with the indicated amount of BMP2). FIG. 26B shows the amount of ectopic bone (BV/TV). Note that selective RARγ antagonist 7c-loaded NP significantly increased rhBMP2 induced bone formation (*$p<0.008$ 0.3 μg BMP2 vs 0.3 μg BMP2+7c-NP; n=4).

REFERENCES

All references listed below and throughout the specification are hereby incorporated by reference in their entirety.
1. Adamo et al. J. Control Release 222:169-175, 2016.
2. Alferiev et al., Biomaterials 51:22-29, 2015.
3. Alferiev et al., United States Patent Publication No, 2013-0296285A1.
4. Baron et al., Anat. Rec. 208(1):137-145, 1984.
5. Cahill et al., J.A.M.A. 302(1):58-66, 2009.
6. Campana et al., J. Mater. Sci. Mater. Med. 25(10):2445-61, 2014.
7. Carragee et al., Spine J. 11(6):471-491, 2011.
8. Chakkalakal et al., J. Bone Miner. Res. 31(9):1666-1675, 2016.
9. Chakkalakal et al., J. Bone Miner. Res. 2016 Notes: 10.1002/jbmr.2820.
10. Chambers et al., Development 134(7):1369-1383, 2007.
11. Chambon, FASEB J 10(9):940-54, 1996.
12. Chandraratna, J. Am. Acad. Dermatol. 39(4 Pt 2):S124-S128, 1998.
13. Chapellier et al., Genesis 32(2):95-98, 2002.
14. Chorny et al., J. Control Release 83(3):389-400, 2002.
15. Chorny et al., J. Control Release 83(3):401-414, 2002.
16. Chorny et al. J. Pharm. Biomed. Anal. 32(1):189-196, 2003.
17. Chorny et al., Biodegradable nanoparticles as drug delivery systems for parenteral administration. In: Yaszemski et al., editors. Tissue Engineering and Novel Delivery Systems. New York: Marcel Dekker; 2003. p. 393-422.
18. Chorny et al., Mol. Ther. 14(3):382-391, 2006.
19. Chorny et al., FASEB J. 21(10):2510-2519, 2007.
20. Chorny et al., Mol. Pharm. 6(5):1380-1387, 2009.
21. Chorny et al., J. Control Release 146(1):144-151, 2010.
22. Chorny et al., Proc. Natl. Acad. Sci. USA 107(18):8346-8351, 2010.
23. Chorny et al., Pharm. Res. 29(5):1232-1241, 2012.
24. Chorny et al., FASEB J. 27(6):2198-2206, 2013.
25. Cunningham et al., Nat. Rev. Mol. Cell. Biol. 16(2):110-123, 2015.
26. Davis et al., Nat. Rev. Drug Discov. 7(9):771-782, 2008.
27. Dev et al., Mol. Cell. Biol. 27(11):4179-4197, 2007.
28. Epstein, Surg. Neurol. Int. 4(Suppl 5):S343-S352, 2013.
29. Epstein, Surg. Neurol. Int. 5(Suppl 15):S552-S560, 2015.
30. Evans and Mangelsdorf, Cell 157(1):255-266, 2014.
31. Fishbein et al., Arterioscler. Thromb. Vasc. Biol. 21(9):1434-1439, 2001.
32. Garnaas et al., Dev. Biol. 372(2):178-189, 2012.
33. Hardwick et al., Nat. Rev. Cancer 8(10):806-812, 2008.
34. Hind and Stinchcombe, Curr. Opin. Invest. Drugs 10(11):1243-1250, 2009.
35. Hoffman et al., J.C.B. 174(1):101-113, 2006.
36. Hood et al., Biomaterials 35(11):3708-3715, 2014.
37. Iwamoto et al., J.C.B. 150(1):27-40, 2000.
38. Iwamoto et al., Dev. Biol. 305(1):40-51, 2007.
39. Le et al., Oncogene 19(11):1457-1465, 2000.
40. Meister et al., Anticancer Res. 18(3A):1777-86, 1998.
41. Minegishi et al., Biochem. Biophys. Res. Commun. 454(1):12-18, 2014.
42. Morrell, Proc. Am. Thorac. Soc. 3(8):680-686, 2006.
43. Katagiri et al., Genes to cells: devoted to molecular & cellular mechanisms 7(9):949-960, 2002.
44. Kimura et al., Cancer Cell 13:249-260, 2008.
45. Peer et al., Nat. Nanotechnol. 2(12):751-760, 2007.
46. Pendaries et al., Oncogene 22(50):8212-8220, 2003.
47. Piskunov et al., Subcell. Biochem. 70:103-127, 2014.
48. Rochette-Egly, Cell Signal 15(4):355-366, 2003.
49. Ronga et al., Injury 44(suppl 1):S34-S39, 2013.
50. Sheng et al., Proc. Natl. Acad. Sci. USA 107(44):18886-18891, 2010.
51. Shimono et al., Nat. Med. 17(4):454-460, 2011.
52. Shimono et al., J. Orthop. Res. 28(2):271-277, 2010.
53. Shore et al., Nat. Genet. 38(5):525-527, 2006.
54. Sieber et al., 20(5-6):343-355, 2009.

55. Sorrentino et al., Evodevo 3(1):22, 2012.
56. Tengood et al., Nanomedicines for Restenosis Therapy. In: V. Torchilin, editor. Handbook of Nanobiomedical Research (Fundamentals, Applications and Recent Developments, v2: Applications in Therapy). London: World Scientific Publishing; 2014. p. 39-87.
57. Tengood et al., Proc. Natl. Acad. Sci. USA 111(11):4245-4250, 2014.
58. Thacher et al., Curr. Pharm. Des. 6(1):25-58, 2004.
59. Uchibe et al., J. Orthop. Res. 2016 Jun. 21. doi: 10.1002/jor.23347.
60. Weston et al., J. Cell Biol. 158(1):39-51, 2002.
61. Williams et al., Dev. Biol, 328(2):315-327, 2009.
62. Williams et al., J. Biol. Chem. 285(47):36674-36681, 2010.
63. Wong et al., Am. J. Respir. Cell. Mol. Biol. 33(5):438-446, 2005.
64. Yagami et al., J.C.B. 147(5):1097-1108, 1999.
65. Yasuhara et al., Lab. Invest. 91(12):1739-1752, 2011.
66. International Patent Publication No. WO 2005/066115 A2.

The invention claimed is:

1. A method of treating a bone growth imbalance in a discrete area of bone in a subject in need thereof, comprising administering a lyophilized nanoparticle pharmaceutical composition which comprises a poly(D,L-lactide) nanoparticle loaded with a retinoic acid receptor gamma (RARγ) modifying agent to the subject by injection,
wherein the subject does not suffer from heterotrophic ossification and wherein the RARγ modifying agent is an RARγ agonist.

2. The method of claim 1, wherein the injection is local injection to a discrete area of bone requiring growth modification.

3. The method of claim 1, wherein the bone growth imbalance is an imbalance of bone length, bone alignment, or both bone length and bone alignment.

* * * * *